United States Patent [19]
Scanlin et al.

[11] Patent Number: 5,948,681
[45] Date of Patent: Sep. 7, 1999

[54] NON-VIRAL VEHICLES FOR USE IN GENE TRANSFER

[75] Inventors: Thomas F. Scanlin; Mary Catherine Glick; Wouter J.W. Kollen, all of Philadelphia, Pa.

[73] Assignee: Children's Hospital of Philadelphia, Philadelphia, Pa.

[21] Appl. No.: 08/907,673

[22] Filed: Aug. 8, 1997

Related U.S. Application Data

[60] Provisional application No. 60/023,941, Aug. 14, 1996.

[51] Int. Cl.$^6$ ................................... C12N 15/64
[52] U.S. Cl. ................... 435/455; 435/320.1; 530/322
[58] Field of Search ................... 435/455, 320.1; 530/322

[56] References Cited

U.S. PATENT DOCUMENTS

| | | | |
|---|---|---|---|
| 4,868,116 | 9/1989 | Morgan et al. | 435/456 |
| 4,897,355 | 1/1990 | Eppstein et al. | 424/450 |
| 4,980,286 | 12/1990 | Morgan et al. | 435/69.1 |
| 5,034,506 | 7/1991 | Summerton et al. | 528/391 |
| 5,166,320 | 11/1992 | Wu et al. | 530/395 |
| 5,240,846 | 8/1993 | Collins et al. | 435/371 |
| 5,380,716 | 1/1995 | Conrad et al. | 514/56 |
| 5,384,128 | 1/1995 | Meezan et al. | 424/450 |
| 5,436,140 | 7/1995 | Kino et al. | 435/71.3 |
| 5,473,054 | 12/1995 | Jameson et al. | 530/328 |
| 5,481,043 | 1/1996 | Wagner et al. | 568/309 |
| 5,516,894 | 5/1996 | Reppert | 530/350 |
| 5,518,880 | 5/1996 | Leonard et al. | 435/6 |
| 5,518,881 | 5/1996 | Gordon et al. | 435/6 |
| 5,536,647 | 7/1996 | Ceriani et al. | 435/69.1 |
| 5,543,399 | 8/1996 | Riordan et al. | 514/21 |
| 5,547,932 | 8/1996 | Curiel et al. | 435/85 |
| 5,552,308 | 9/1996 | Hoffman et al. | 435/455 |
| 5,552,309 | 9/1996 | March | 435/456 |
| 5,556,953 | 9/1996 | Zhang et al. | 536/23.74 |
| 5,559,132 | 9/1996 | Miller | 514/329 |
| 5,571,797 | 11/1996 | Ohno et al. | 514/44 |
| 5,589,568 | 12/1996 | Higashijima et al. | 530/324 |
| 5,595,897 | 1/1997 | Midoux et al. | 435/458 |
| 5,610,019 | 3/1997 | Day et al. | 435/7.1 |
| 5,610,140 | 3/1997 | Goodfellow et al. | 514/15 |
| 5,631,236 | 5/1997 | Woo et al. | 514/44 |
| 5,635,383 | 6/1997 | Wu et al. | 435/458 |

FOREIGN PATENT DOCUMENTS

| | | |
|---|---|---|
| WO93/12240 | 6/1993 | WIPO. |
| WO 95/30020 | 11/1995 | WIPO. |

OTHER PUBLICATIONS

Ballard, 1996, *J. of Perinatology* 16(2):S28–S34.
Barondes, 1994, *Cell* 76:597–598.
Brasier et al., 1989, *Biotechniques* 7:1116–1123.
Canonico, 1997, Gene Therapy for Chronic Inflammatory Diseases of the Lungs in *Gene Therapy for Diseases of the Lung*, K.L. Brigham, ed, Marcel Dekker, New York, pp. 285–307.
Collins, 1997, Discovering Genes That Cause Disease in *Gene Therapy for Diseases of the Lung*. K.l. Brigham, ed. (Marcel Dekker, NY), pp. 17–26.
Crystal et al., 1995, *Science* 270:404–410.
Curiel et al., 1991, *Proc. Natl. Acad. Sci. USA* 88:8850–8854.
Curiel et al., 1996, *Am. J. Respir. Cell Mol. Biol.* 14:1–18.
De Wet et al., 1987, *Mol. Cell. Biol.* 7:725–737.
Derrien et al., 1989, *Glycoconjugate J.* 6:241–255.
Diamond et al., 1991, *J. Biol. Chem.* 266:22761–22769.
Drickamer et al., 1993, *Annu. Rev. Cell Biol.* 9:237–264.
Drumm et al., 1990, *Cell* 62:1227–1233.
Engelhardt et al., 1992, *J. Clin. Invest.* 90:2598–2607.
Erbacher, et al., 1996, *Experimental Cell Research* 225186–194.
Erbacher et al., 1996, *Hum. Gene Ther.* 7:721–729.
Erbacher et al., 1995, *Bioconj. Chem.* 6:401–410.
Fasbender et al., 1995, *Am. J. Physiol.* 269:L45–L51.
Fiume et al, 1994, *Biochem. Pharmacol.* 47:643–650.
Gao et al., 1993, *Human Gene Therapy* 4:17–24.
*Gene. Eng. News* 17(12):26 Jun. 15, 1997.
Gottshalk et al., 1996, *Gene Ther.* 3:448–457.
Harris, et al., 1993, *Am.J. Respir Cell Mol. Biol.* 9:441–447.
Howard et al., 1995, *Am J. Physiol.* 269:1565–1576.
Jetten et al., 1989, *Science* 244:1472–1475.
Lane et al., 1996, *Pediatric Research* 39:390–394.
Levine, 1964, *Proc. Soc. Exp. Biol. Med.* 116:1127–1131.
Lisby et al., 1996, *Pediatr. Res.* 39:389A.
Lowry et al., 1951, *J. Biol. Chem.* 193:265–275.
Marks et al., 1988, *10th International CF Congress*, Sydney, Australia.
Marsh et al., 1997, *Nature Genetics* 15:389–392.
Martinez–Fong et al., 1994, *Hepatology* 20:1602–1608.
Matteucci et al., 1996, *Nature* 384:20–22.
Midoux et al., 1993, *Nucleic Acids Res.* 21:871–878.
Monsigny et al., 1988, *Analytical BioChem.* 175:525–530.
Monsigny et al., 1988, *Biochimie* 70:1633–1649.
Monsigny et al., 1984, *Biol. Cell* 51:187–196.
Mulberg et al., 1994, *NeuroReport* 5:1684–1688.
Nielsen et al., 1991, *Science* 254: 1497.
Nogee et al. 1994, *J. Clin. Invest.* 93:1860–1863.
Olsen et al., 1992, *Human Gene Therapy* 3:253–266.
Reddel et al., 1988, *Cancer Res.* 48:1904–1909.
Rundle, *Sequana to Unveil Discovery of Gene Related to Asthma, Wall Street J.*, May 21, 1997.
Santos et al., 1994, *Biochim. Biophys. Acta* 1195:96–102.
Scanlin et al., 1988, A.P. Fishman, ed. (McGraw–Hill, New York) pp. 1273–1294.
Sekhon et al., 1995, *Nature Med.* 1:1201–1203.
Simon et al., 1993, *Human Gene Therapy* 4:771–780.

(List continued on next page.)

*Primary Examiner*—James Ketter
*Attorney, Agent, or Firm*—Panitch Schwarze Jacobs & Nadel, P.C.

[57] ABSTRACT

The invention relates to a compositions and methods for transfection of cells, particularly airway epithelial cells, with DNA complexed to polylysine substituted with glycosyl residues. The invention also relates to methods of treating humans having respiratory disease comprising administering to a human the composition of the invention.

29 Claims, 19 Drawing Sheets

OTHER PUBLICATIONS

St. George et al., 1995, "Efficacy of Adenoviral Vectors in Airway Epithelium" Cystic Fibrosis Conference, Abstract #151.

Thurnher et al., 1994, Glycobiology 4:429–435.

Venglarik et al., 1990, *Am. J. Physiol.* 259:C358–C364.

Vogel, 1997, *Science* 276:1327.

Vogel, 1997, *Science* 276:1643–1646.

Wadhwa et al., 1995, *Bioconj. Chem.* 6:283–291.

Wagner et al., 1992, *Proc. Natl. Acad. Sci. USA* 89:7934–7938.

Wei et al. 1996, J. Cell. Physiol. 168:001–0012.

Welsh et al., 1995, Scriber et al., eds. (McGraw–Hill, New York) pp. 3799–3876.

Whitsett et al., 1995, Physiological Reviews 75:749–757.

Wilson et al., 1992, *J. Bio Chem.* 267:pp. 963–967.

Wilson, 1995, *J. Clin. Invest.* 96:2547–2554.

Wu et al., 1990, *Am. J. Respir. Cell Mol. Biol.* 3:467–478.

Yang et al., 1993, *Hum. Mol. Gen.* 8:1253–1261.

Zielenski et al., 1996, *Pediatric Pulmonology* 13:A151.

RLU per mg protein

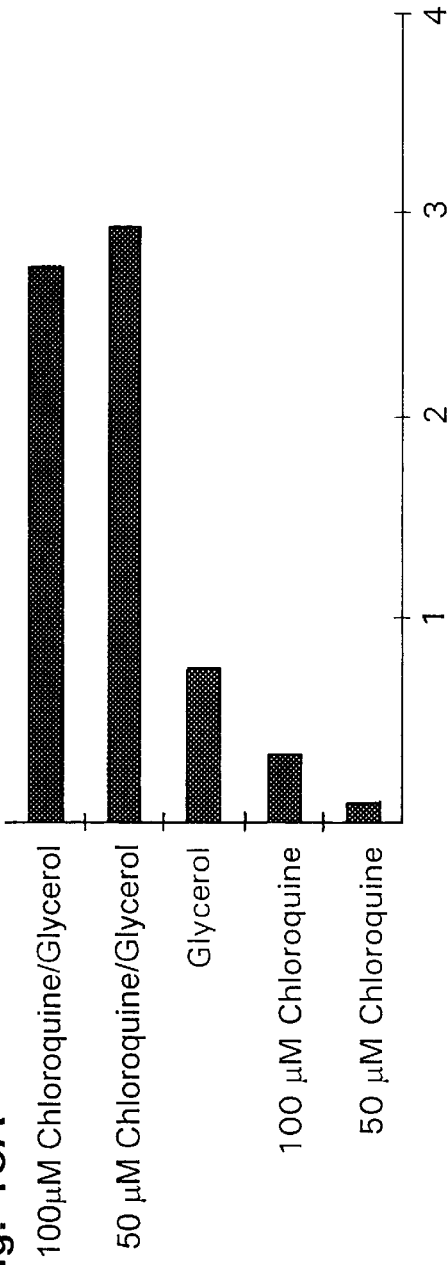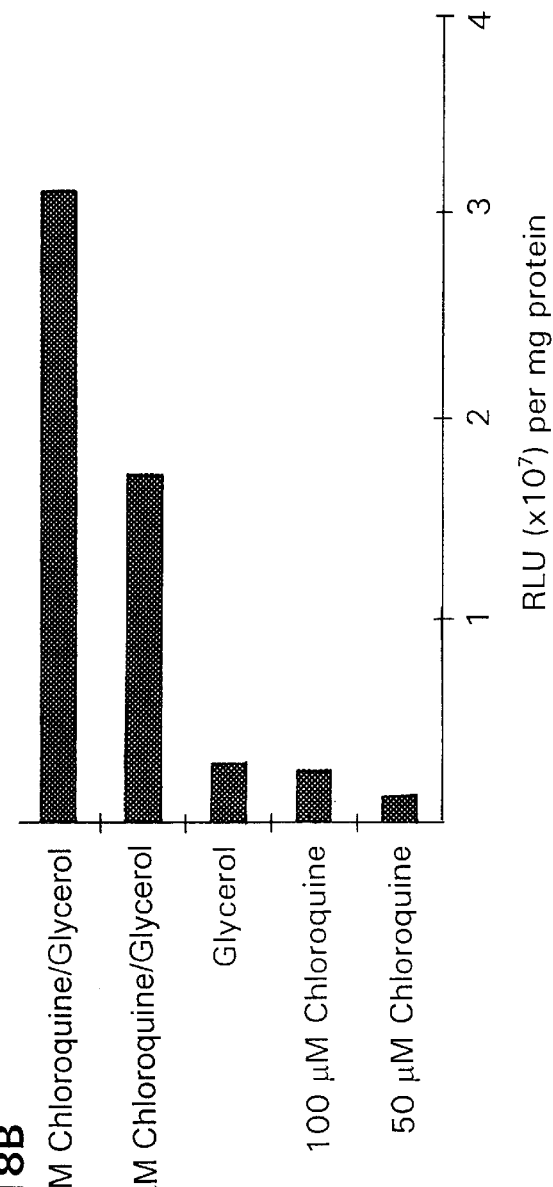

NON-VIRAL VEHICLES FOR USE IN GENE TRANSFER

CROSS REFERENCE TO RELATED APPLICATIONS

This invention claims priority under 35 U.S.C. § 119(e) to U.S. Provisional Application No. 60/023,941, filed on Aug. 14, 1996.

GOVERNMENT SUPPORT

Portions of this invention were supported by a grant from the U.S. Government NIH Grant No. RO1 16859) and the U.S. Government may therefore have certain rights in the invention.

FIELD OF THE INVENTION

The field of the invention is delivery of genes to cells in vitro and in vivo, in particular, non-viral delivery of genes to cells.

BACKGROUND OF THE INVENTION

Diseases of the respiratory tract are among the most common diseases in humans and range in severity from being merely mild and annoying to life threatening. Examples of severe to life threatening respiratory diseases in humans include cystic fibrosis, asthma, emphysema, idiopathic pulmonary fibrosis and congenital deficiency of surfactant protein. Each of these diseases is suitable for gene therapy as a means of treatment provided that a gene delivery vehicle is available which delivers the appropriate gene in an effective and non-toxic manner. Gene therapy approaches which have been used or are contemplated for treatment of these respiratory diseases are reviewed in Canonico (1997, Gene Therapy for Chronic Inflammatory Diseases of the Lungs in *Gene Therapy for Diseases of the Lung*, K. L. Brigham, ed, Marcel Dekker, N.Y., pp.285–307).

Cystic fibrosis (CF) is the most common lethal genetic disease in Caucasians and, although the average life expectancy has increased to approximately 30 years in the past decade, there remains no effective cure for CF (Scanlin et aL, 1988, A. P. Fishman, ed. (McGraw-Hill, N.Y.) pp. 1273–1294; Welsh et al., 1995, Scriber et al, eds. (McGraw-Hill, N.Y.) pp. 3799–3876).

Patients having CF encode a mutated cystic fibrosis transmembrane conductance regulator (CFTR) gene. Although CF is a multisystem disease, the most important and life threatening pathology occurs in the lung. Gene therapy has been proposed as a means of developing effective therapy to combat the pathology of CF. However, there are a plethora of problems associated with this approach, not the least of which is the lack of a suitable vehicle for delivery of the CFTR gene to humans.

Initial reports of gene therapy as a means of treating CF have focussed on airway epithelial cells as targets for the CFTR gene. Viral vectors have been used as vehicles for delivery of the CFTR gene to these cells in humans. However, the vectors themselves have proved to be sufficiently immunogenic so as to diminish any positive effect of the successful delivery of the CFTR gene to the affected cells of the individual (Wilson, 1995, *J. Clin. Invest.* 96:2547–2554; Crystal et al., 1995, *Science* 270:404–410).

Other vehicles which have been used as gene delivery vehicles include cationic lipids for transfer of genes to airway epithelial cells (Fasbender et al., 1995, *Am. J. Physiol.* 269:L45–L51). In addition, polylysines (poly-L-lysine) complexed with various glycoproteins, including transferrin targeted to the transferrin receptor, have been examined (Curiel et al., 1991, *Proc. Natl. Acad. Sci. USA* 88:8850–8854). Also reported, is the use of asialoglycoproteins targeted to hepatic cells through the asialoglycoprotein receptor (Wilson et al., 1992, *J. Biol. Chem.* 267:963–967), and the use of Tn antigen for gene transfer (Thurnher et al., 1994, *Glycobiology* 4:429–435). The above-referenced studies have largely been performed in cells other than airway epithelial cells. Moreover, complexes having glycoprotein as a component thereof are potentially immunogenic and therefore may not be of immediate value in human gene therapy.

Asthma is a disease of the industrialized 20th century, being described for the first time in the mid- 1800's. Exposure to otherwise harmless pollens and other allergens may set off a life threatening asthma attack in susceptible individuals, wherein constriction of the bronchioles renders a patient virtually unable to breathe. Asthma attacks are triggered by exposure to allergens which cause activated T lymphocytes of the $T_H2$ subset to secrete cytokines, primarily interleukin 4 (IL-4) and interleukin 5 (IL-5) setting off a cascade of events which ultimately leads to bronchioconstriction. IL-4 induces production by activated B lymphocytes of immunoglobulin (Ig) E which, in turn, induces the production of histamine from mast cells. IL-5 triggers the production by eosinophils of small fatty molecules known as leukotrienes. The combined action of histamine and leukotrienes causes blood vessels to leak and lung tissues to swell. The smooth muscles of the airways constrict and mucus production is induced which serves to further clog the already constricted airways.

Current asthma therapy is aimed at treating the end result, i.e., the airway constriction. However, targets other than the end point may be more amenable to therapy, particularly gene therapy. In addition, asthma is believed to have a genetic component, and in fact, the identification of an asthma gene has recently been announced (Vogel, 1997, *Science* 276:1327). This disease is therefore suitable for treatment using a gene therapy approach.

Alpha$_1$ antitrypsin ($\alpha$1AT) deficiency, like CF, is an inherited monogenic disorder having virtually no effective therapy beyond treatment for alleviation of the symptoms of the disease. $\alpha$1AT deficiency is primarily associated with emphysema, a lung disease characterized by unopposed elastolytic destruction of the lung parenchyma. Although $\alpha$1AT is synthesized primarily in liver cells, functional $\alpha$1AT is responsible for over 95% of the antiprotease protection in the lower respiratory system. The most common genetic abnormality associated with premature emphysema is the Z allele. In this mutant allele, a lysine is substituted for glutamic acid at amino acid position 342 in $\alpha$1AT, thereby altering the three dimensional configuration of the protein and affecting secretion of the protein from the cells in which it is synthesized. Other mutant alleles of the $\alpha$1AT gene also contribute to the disease, and irrespective of the genetic abnormality, a critical threshold of an $\alpha$1AT serum level of less than 10 $\mu$M appears necessary for an individual to develop pulmonary emphysema.

Both the liver and the lung have been targeted for gene therapy as a means of treating $\alpha$1AT deficiency. With respect to the liver, although successful liver-directed $\alpha$1AT gene therapy has been achieved using various strategies, serum $\alpha$1AT levels in all of these systems were below what would be necessary for physiological correction of the deficiency. Adenovirus-mediated gene therapy directed to lung cells has been attempted. However, because of the problems associated with adenovirus-induced inflammation, this is not the preferred approach. The use of other viruses and of liposomes has also been contemplated as a means of delivering α1AT to lung cells (Canonico, supra).

Idiopathic pulmonary fibrosis (IPF) is a lethal disease with a median time from diagnosis to death of 3 to 5 years. Since, current therapies for IPF have marginal effect on improved lung function or overall survival, a gene therapy approach for treatment of this disease is justified. In IPF, an inflammatory response to an unidentified insult or injury occurs following an exuberant fibrotic response. The initial inflammatory response is predominantly neutrophilic but evolves to a predominant lymphocytic and monocytic response. As yet, no specific genetic defect has been identified; however, gene therapy targeted to specific sites in the disease pathway, has been contemplated. For example, antisense therapy targeting specific growth factors or cytokines implicated in IPF has been proposed, in addition to delivery of other genes such as the cyclo-oxygenase-2 gene, the latter of which may block the effects of certain proinflammatory cytokines (Canonico, supra).

Congenital deficiency of surfactant protein results in severe respiratory disease in infants. The fundamental importance of surfactant protein (SP)-B in pulmonary function has been elucidated from studies on infants unable to produce SP-B due a genetic defect which gives rise to a lethal neonatal respiratory disease. Respiratory failure in these infants was refractory to therapies which included mechanical ventilation, surfactant replacement and extracorporeal membrane oxygenation. A genetically based deficiency in production of a second surfactant protein, SP-C, may also contribute to the development of this disease. Since this disease is governed by genes which have been identified and in view of the absence of any effective current therapy for this disease, a gene therapy approach for treatment of SP-B and/or SP-C deficiency seems appropriate. For a discussion on congenital deficiency of surfactant protein, see Whitsett et al. (1995, Physiological Reviews 75:749–757) and Nogee et al. (1994, J. Clin. Invest. 93:1860–1863).

As an alternative to virus or lipid mediated gene therapy, it has been reported that substitution of polylysine with lactose residues facilitates a high level of transfection of HepG2 cells via galactose-specific membrane lectins (Midoux et al., 1993, Nucleic Acids Res. 21:871–878; Erbacher et al., 1995, Bioconj. Chem. 6:401–410). It is also known that partially gluconoylated polylysine is an efficient vehicle for reporter gene expression in a number of different cell types (Midoux et al. ,1995, International Application Publication No. WO 95/30020; U.S. Pat. No. 5,595,897).

Polylysine substituted with specific sugars such as mannose or fucose may be used to transfect human macrophages which have a membrane lectin for mannose and fucose (Erbacher et al, 1996, Hum. Gene Ther. 7:721–729). Further, complex asialo-oligosaccharides coupled to short polylysine polymers have been used to transfect DNA into HepG2 cells (Wadhwa et al., 1995, Bioconj. Chem. 6:283–291).

There remains an acute need for a suitable vehicle for delivery of genes to respiratory cells, which vehicle must be non-immunogenic. Given the paucity of information on the nature of endogenous lectins on human airway epithelial cells (Drickamer et al., 1993, Ann. Rev. Cell Biol. 9:237–264), the use of polylysine derivatized with specific carbohydrates for delivery of genes to airway epithelial cells could not be predicted to successfully facilitate introduction of genes into these cells.

SUMMARY OF THE INVENTION

The invention relates to a method of transfecting airway epithelial cells comprising adding to the cells a composition comprising a complex comprising an isolated nucleic acid and a glycosylated polylysine.

There is also provided in the invention a method of transfecting airway epithelial cells, the method comprising generating a composition comprising a complex comprising an isolated nucleic acid and a glycosylated polylysine, and adding the complex to the airway epithelial cells.

In one aspect, the composition further comprises at least one of chloroquine, glycerol and a fusogenic peptide.

In another aspect, the glycosylated polylysine has a sugar component selected from the group consisting of lactose, α-glucose, β-galactose, mannose, mannose-6-phosphate, fucose and N-acetylglucosamine. Preferably, the glycosylated polylysine is lactosylated polylysine.

In one embodiment, the cells are transfected in vitro and in another embodiment, the cells are transfected in vivo.

In yet other embodiments, the isolated nucleic acid is DNA or cDNA. The DNA may be selected from the group consisting of DNA encoding CFTR, an asthma gene, DNA encoding α1AT, a gene affecting idiopathic pulmonary fibrosis, DNA encoding SP-B and DNA encoding SP-C. Preferably, the DNA encodes CFTR.

In another embodiment, the DNA is antisense DNA capable of inhibiting the expression of a gene, which gene is required for the development of a respiratory disease in a mammal.

In preferred embodiments, the gene is selected from the group consisting of an interleukin gene and a gene affecting leukotriene synthesis. More preferably, the respiratory disease is asthma and the gene is a gene encoding IL-4 or a gene encoding IL-5.

The invention also includes a pharmaceutical composition for treatment of a respiratory disease in a human. The composition comprises a complex comprising an isolated nucleic acid encoding a protein, or a biologically active fragment thereof, and a glycosylated polylysine, wherein the isolated nucleic acid is DNA selected from the group consisting of DNA encoding CFTR, an asthma gene, DNA encoding α1AT, a gene affecting idiopathic pulmonary fibrosis, DNA encoding SP-B and DNA encoding SP-C, the complex being suspended in a pharmaceutically acceptable carrier, the complex being capable of transfecting airway epithelial cells when added thereto.

The pharmaceutical composition may further comprise at least one of chloroquine, glycerol and a fisogenic peptide.

In one embodiment, the respiratory disease is selected from the group consisting of cystic fibrosis, asthma, emphysema, idiopathic pulmonary fibrosis and congenital deficiency of surfactant protein.

In another embodiment, DNA comprises cDNA, which preferably encodes CFTR.

In yet another embodiment, the glycosylated polylysine has a sugar component selected from the group consisting of lactose, α-glucose, β-galactose, mannose, mannose-6-phosphate, fucose and N-acetylglucosamine. Preferably, the glycosylated polylysine comprises lactosylated polylysine.

In a preferred embodiment, about 10% to about 60% of the amino groups of the polylysine have a lactose molecule substituted thereon. More preferably, about 12% to about 40% of the amino groups of the polylysine have a lactose molecule substituted thereon.

In yet another preferred embodiment, the weight to weight ratio of lactosylated polylysine to DNA in the complex is about one to one to about fifteen to one.

There is further provided in the invention a pharmaceutical composition for treatment of a respiratory disease in a human comprising a complex comprising an isolated nucleic acid and a glycosylated polylysine, wherein the isolated nucleic acid comprises antisense DNA capable of inhibiting the expression of a gene, which gene is required for the development of a respiratory disease in a mammal.

In one embodiment of this aspect of the invention, gene is selected from the group consisting of an interleukin gene and a gene affecting leukotriene synthesis. Preferably, the respiratory disease is asthma and the gene is a gene encoding IL-4 or IL-5.

The pharmaceutical composition may further comprise at least one of chloroquine, glycerol and a fusogenic peptide.

In addition, the glycosylated polylysine in the pharmaceutical composition may have a sugar component selected from the group consisting of lactose, α-glucose, β-galactose, mannose, mannose-6-phosphate, fucose and N-acetylglucosamine. Preferably, the glycosylated polylysine comprises lactosylated polylysine. More preferably, about 10% to about 60% of the amino groups of the polylysine have a lactose molecule substituted thereon. Even more preferably, about 12% to about 40% of the amino groups of the polylysine have a lactose molecule substituted thereon.

In another preferred embodiment, the weight to weight ratio of lactosylated polylysine to DNA in the complex is about one to one to about fifteen to one.

The invention also includes a lactosylated polylysine nucleic acid complex comprising DNA encoding CFTR, or a biologically active fragment thereof, and lactosylated polylysine, wherein about 10% to about 60% of the amino groups of the polylysine have a lactose molecule substituted thereon, and the weight to weight ratio of lactosylated polylysine to the DNA in the complex is about one to one to about fifteen to one, the complex being capable of transfecting airway epithelial cells when added thereto. Preferably, the weight to weight ratio of lactosylated polylysine to the isolated nucleic acid in the complex is about nine to one.

Also included in the invention is a kit comprising an isolated nucleic acid encoding CFTR, or a biologically active fragment thereof, a glycosylated polylysine and instructions for using the kit for transfection of airway epithelial cells.

In addition, the invention includes a kit comprising an isolated nucleic acid encoding CFTR, or a biologically active fragment thereof, a glycosylated polylysine and instructions for using the kit for treatment of cystic fibrosis in a human patient.

The invention further relates to a method of treating a human patient having cystic fibrosis, the method comprising administering to the human a pharmaceutical composition comprising a complex comprising an isolated nucleic acid encoding CFTR, or a biologically active fragment thereof, and a glycosylated polylysine. The composition may further comprise at least one of chloroquine, glycerol and a fusogenic peptide.

In a preferred embodiment of this aspect of the invention, the pharmaceutical composition is administered to the human by a means selected from the group consisting of aerosol nebulizer, bronchoscopy and injection in utero.

In yet another preferred embodiment of this aspect of the invention, the isolated nucleic acid comprises DNA, preferably, cDNA.

In another aspect of this method of the invention, the glycosylated polylysine has a sugar component selected from the group consisting of lactose, α-glucose, β-galactose, mannose, mannose-6-phosphate, fucose and N-acetylglucosamine. Preferably, the glycosylated polylysine comprises lactosylated polylysine. More preferably, about 10% to about 60% of the amino groups of the polylysine have a lactose molecule substituted thereon. Also more preferably, the weight to weight ratio of lactosylated polylysine to DNA in the complex is about one to one to about fifteen to one. Even more preferably, the weight to weight ratio of lactosylated polylysine to DNA in the complex is about three to one to about nine to one.

There is further included in the invention a method of identifying a test compound capable of modulating the activity of CFTR. The method comprises transfecting airway epithelial cells in the presence or absence of the test compound with a complex comprising an isolated nucleic acid encoding CFTR, or a biologically active fragment thereof, and a glycosylated polylysine, and measuring the activity of CFTR in the cells, wherein a higher or a lower level of CFTR activity in the presence of the test compound compared with CFTR activity in cells in the absence of the test compound is an indication that the test compound is capable of modulating the activity of CFTR.

The invention includes a compound identified according to the just described method.

In addition, the invention relates to an in vitro cell transfection kit comprising a selection of glycosylated polylysines and instructions for using the kit. The kit may further comprise a reporter DNA and may also further comprise at least one of chloroquine, glycerol and a fusogenic peptide.

Preferably, the glycosylated polylysine in the kit has a sugar component selected from the group consisting of lactose, α-glucose, β-galactose, mannose, mannose-6-phosphate, fucose and N-acetylglucosamine.

Also preferably, the reporter DNA is selected from the group consisting of a chloramphenicol acetyl transferase gene, a luciferase gene, a green fluorescent protein gene, and a β-galactosidase gene.

The invention also includes a nebulizer having a composition comprising a complex comprising an isolated nucleic acid and a glycosylated polylysine placed therein. Preferably, the isolated nucleic acid is DNA encoding CFTR and the glycosylated polylysine is lactosylated polylysine.

In addition, the invention includes a bronchoscope having a composition comprising a complex comprising an isolated nucleic acid and a glycosylated polylysine placed therein. Preferably, the isolated nucleic acid is DNA encoding CFTR and the glycosylated polylysine is lactosylated polylysine.

There is further included in the invention an airway epithelial cell transfected with a complex comprising an isolated nucleic acid and a glycosylated polylysine. Preferably, the isolated nucleic acid is DNA encoding CFTR and the glycosylated polylysine is lactosylated polylysine.

In addition, the invention includes a composition for transfection of airway epithelial cells comprising a complex comprising an isolated nucleic acid and a lactosylated polylysine, wherein the isolated nucleic acid is DNA selected from the group consisting of DNA encoding CFTR, an asthma gene, DNA encoding α1AT, a gene affecting idiopathic pulmonary fibrosis, DNA encoding SP-B and DNA encoding SP-C. The composition may further at least one of chloroquine, glycerol and a fusogenic peptide.

In a preferred embodiment, the DNA is DNA encoding CFTR.

Preferably, the airway epithelial cells are transfected in vitro or are transfected in vivo.

BRIEF DESCRIPTION OF THE DRAWINGS

FIG. 2, comprising parts A and B, is a series of graphs depicting the relationship between the concentration of plasmid and cell number and transfected gene expression.

FIG. 3, comprising parts A and B, is a series of graphs depicting the effect of transfection time on luciferase gene expression (A) and the effect of incubation time post transfection on luciferase gene expression (B) following transfection of CF/T43 cells using gluconoylated polylysine as a vehicle.

FIG. 5, comprising parts A, B and C, is a series of graphs depicting optimization of expression of a reporter gene in transfected CF/T43 cells using lactosylated polylysine as a vehicle.

FIG. 15 is a series of graphs depicting assays for Cl$^-$ efflux using $^{125}$I. A concentration of 2×$10^5$ cells were cultured in 15 mm wells for three to four days. The cells were washed and $^{125}$I was added in efflux medium, following which, 1 ml fractions were obtained from the cultures. A mixture comprising 20 mM forskolin, 250 mM cAMP and 500 mM isobutyl-1-methylxanthine. (IBMX) was added to the cultures at the time indicated by the arrow, and removal of 1 ml fractions from the cultures at the indicated times was continued. Efflux was measured and was expressed as the rate per minute as described in Santos et al. (1994, *Biochim. Biophys. Acta* 1195:96–102).

FIG. 16 is a series of images of photomicrographs demonstrating high efficiency expression of β-galactosidase following transfection with pCMVLacZ. The efficiency of gene transfer into CF/T43 cells was examined using 60 μg of lactosylated polylysine complexed to 20 μg of pCMVLacZ in the presence of 100 μM chloroquine and 5% glycerol. The cells were transfected for four hours at 37° C. either once or three times on three sequential days, followed by incubation in growth medium. Expression of LacZ was detected following fixation in 2% paraformaldehyde/0.2% glutaraldehyde followed by incubation for 18 hours at 37° C. in X-gal stain. The cells were subsequently examined in a Nikon Diaphot 300 microscope (12.5×magnification).

FIG. 17 is a series of images of photomicrographs of cells depicting expression of CFTR in CF airway epithelial cells in primary culture. Expression of CFTR was detected by in situ hybridization.

FIG. 18 is a series of graphs depicting the effect of potentiating agents on human airway epithelial cell lines. FIG. 18A: BEAS2B, immortalized nonCF airway epithelial cells.; FIG. 18B: CF/T1 (wild type) immortalized airway epithelial cells obtained from a CF patient having the ΔF508 mutation. These cells were previously transfected with wild type CFTR and were subsequently transfected with pCMVLuc/lactosylated polylysine at a DNA to lactosylated polylysine ratio of 1:3 and the indicated concentrations of chloroquine with or without 5% glycerol.

DETAILED DESCRIPTION OF THE INVENTION

Figure 1:
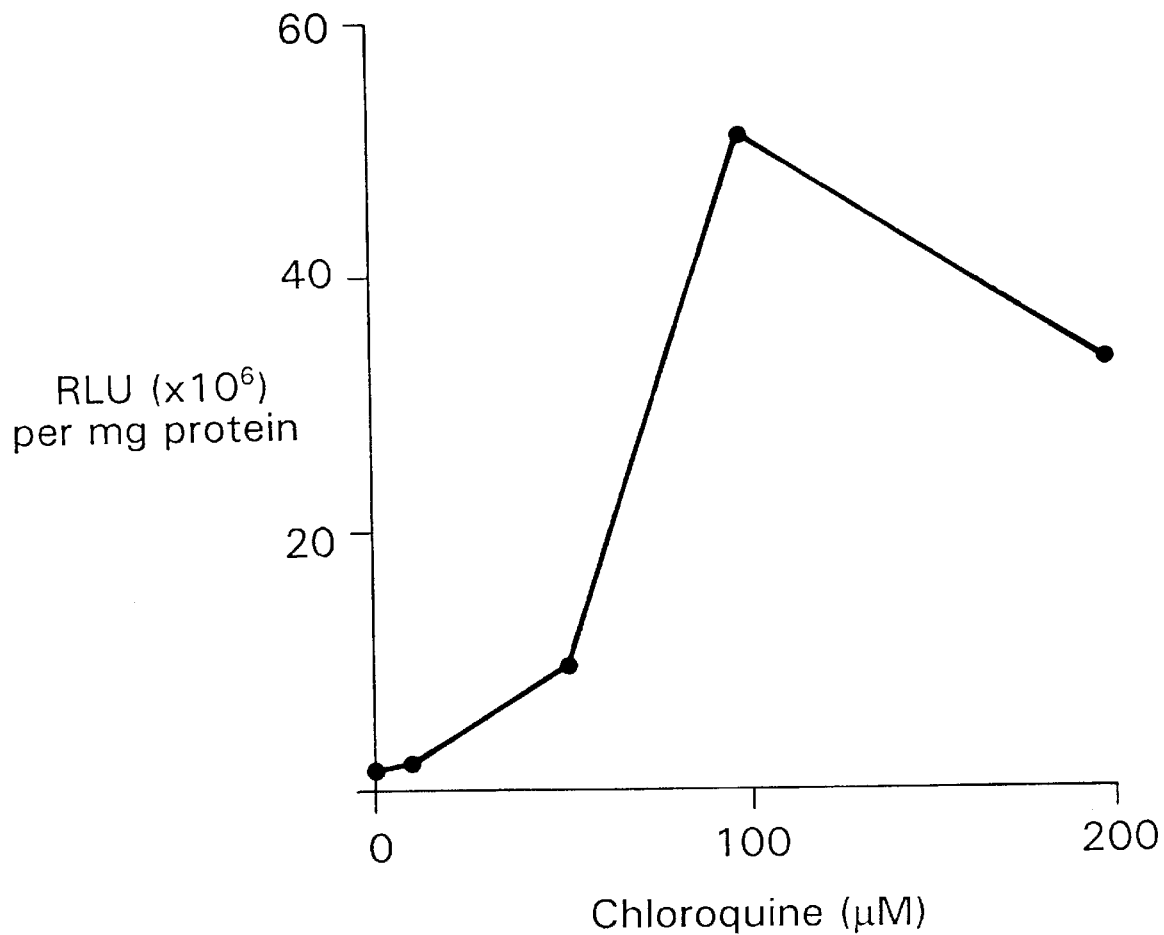
FIG. 1 is a graph depicting the influence of chloroquine on gene expression. Chloroquine at the indicated concentrations, was added to transfection medium containing gluconoylated polylysine and the plasmid pUT 650. The mixture was added to CF/T43 cells which were then incubated for 4 hours. Following subsequent culture of the cells for 48 hours in KGM medium (Clonetics Corp.), the cells were lysed and the level of expression of luciferase was assessed using a luminometer. The relative light units (RLU) were measured at 5 s and the amount of RLU per mg of protein was calculated. When cells were incubated in the absence of chloroquine, $6.8 \times 10^5$ RLU per mg of protein was detected.

It has been discovered that substituted polylysines are capable of facilitating gene delivery to airway epithelial cells thereby providing an alternative to viral vectors for the delivery of genes into airway epithelial cells in patients having respiratory disease. Until the present invention, it was not known that airway epithelial cells could be transfected with DNA complexed to substituted polylysine. The substituted polylysines useful in the present invention comprise polylysine which is partially neutralized by blocking a number of positive-charged residues with sugar groups.

It has been discovered that polylysine substituted with α-glucose, β-galactose or lactose are equally efficient as DNA transfer vehicles for the introduction of DNA into immortalized airway epithelial cells. However, polylysine substituted with lactose is superior to other substituted polylysines for effecting transfer of DNA into primary airway epithelial cells.

Thus, the invention includes a substituted polylysine which comprises either mono or disaccharide residues on a specified number of amino groups.

The use of polylysine substituted with mono or disaccharides for gene delivery is superior compared with other polylysine derivatives and compared with viral vectors in that mono or disaccharide substituted polylysine is non-immunogenic (Levine, 1964, *Proc. Soc. Exp. Biol. Med.* 116:1127–1131; Fiume et al,. 1994, *Biochem. Pharmacol.* 47:643–650).

The generation of substituted polylysine derivatives is well known in the art and is described, for example, in Midoux et al. (supra) and in Martinez-Fong et al., 1994, *Hepatology*, 20:1602–1608). A detailed description of the generation of substituted polylysine derivatives is provided herein in the experimental details section.

To form a substituted polylysine DNA complex, the substituted polylysine derivative is added to DNA in a controlled manner in order that precipitation of the complex so formed does not occur. Generally, an amount of substituted polylysine is added to DNA in solution at a rate of several microliters per about 30 to about 60 seconds. Although, the examples provided in the experimental details section herein recite the rate of addition of substituted polylysine to DNA as being 15 μl per 30 to 60 seconds, it will be appreciated that this rate may vary depending upon the precise amounts and types of substituted polylysine and DNA being mixed.

The types of substituted polylysine which are suitable for transfection of cells will vary depending on the cells to be used. When the polylysine DNA complex is to be used for transfection of airway epithelial cells in vivo in a mammal, preferably a human, then lactosylated polylysine is the polylysine derivative of choice. In contrast, in the case of immortalized airway epithelial cells, lactose, α-glucose, β-galactose, mannose, mannose-6-phosphate, fucose or N-acetylglucosamine substituted polylysine may be used. Similarly, as will be described herein in greater detail, when cells which are not airway epithelial cells are to be transfected, glycosyl residues other than lactose may be used.

By the use of the term "glycosylated polylysine" as used herein, is meant a polylysine molecule which has substituted thereon glycosyl moieties. Thus, the term "glycosylated polylysine" may be distinguished from the term "gluconoylated polylysine" since a gluconoylated polylysine molecule has substituted thereon gluconoyl moieties. Glycosyl moieties differ from gluconoyl moieties in that glycosyl moieties comprise sugar, i.e., carbohydrate molecules, whereas gluconoyl moieties are not considered in the art to be carbohydrate molecules since the characteristic ring structure is open. There are no gluconoyl moieties on the glycosylated polylysine molecules of the present invention.

It has been discovered in the present invention that substitution of about 10% to about 60% of the amino groups of the polylysine molecule with glycosyl residues results in high efficiency transfection of cells. Preferably, substitution of about 12% to about 40% of the amino groups of the polylysine molecule with glycosyl residues is optimal for transfection of cells.

It has been discovered in the present invention that the efficiency by which airway epithelial cells are transfected with nucleic acid complexed with substituted polylysine is affected by the weight to weight ratio of polylysine to DNA. Thus, in the case of polylysine substituted with lactose, preferably, the weight to weight ratio of lactosylated polylysine to DNA ranges from about one to one to about fifteen to one. More preferably, the weight to weight ratio of lactosylated polylysine to DNA ranges from about two to one to about nine to one. Even more preferably, the weight to weight ratio of lactosylated polylysine to DNA ranges from about three to one to about nine to one. When polylysine is substituted with sugars other than lactose, it will be appreciated that the weight to weight ratio of substituted polylysine to DNA will vary depending upon the type of sugar and the type and/or the size of the DNA being used. It is anticipated that the weight to weight ratio of substituted polylysine to DNA will be generally within the ranges given for lactosylated polylysine; however, the invention should not be construed as being limited to these ratios when glycosyl sugars other than lactose are used.

When transfection of cells in vivo in a mammal is contemplated, the type of DNA to be transfected will depend upon the disease to be treated. For example, for treatment of CF, a DNA molecule comprising the CFTR gene, or a biologically active fragment thereof, will be used. When the disease to be treated is asthma, a DNA molecule, or a biologically active fragment thereof, comprising a gene whose protein product serves to alleviate asthma will be used.

By the term "an asthma gene" as used herein, is meant a gene whose protein product has the effect of alleviating asthma. Such genes include those involved in the cascade of events leading to an asthma attack, as well as known or heretofore unknown genes which may be involved in the susceptibility of some individuals to asthma. Genes which are involved in the asthma cascade include genes encoding cytokines, such as, but not limited to, IL-4 and IL-5, genes affecting leukotriene synthesis, genes encoding proteins which govern the production of histamine, and the like. Thus, any gene having the desired effect of alleviating asthma is included in the definition of an asthma gene as used herein.

When the disease to be treated is idiopathic pulmonary fibrosis, a DNA molecule, or a biologically active fragment thereof, comprising a gene whose protein product serves to alleviate idiopathic pulmonary fibrosis will be used.

By the term "a gene affecting idiopathic pulmonary fibrosis" as used herein, is meant a gene which is involved in the events leading to the onset or maintenance of this disease. Similar to the situation with respect to asthma, any gene having the desired effect of alleviating idiopathic pulmonary fibrosis is included in the definition of a gene affecting idiopathic pulmonary fibrosis as used herein.

In the case of emphysema, DNA comprising α1AT, or a biologically active fragment thereof, will be used to transfect cells and, in the case of congenital deficiency of surfactant protein, DNA comprising SP-B and/or SP-C will be used.

The various sources of known DNA's which may be used are either described or are referenced herein. For example, a source of CFTR DNA is described herein in the experimental examples section. A source of α1AT DNA is referenced in Canonico (supra) and a source of SP-B and SP-C DNAs is referenced in Whitsett et al. (1995, Physiological Reviews 75:749–757) and Nogee et al. (1994, J. Clin. Invest. 93:1860–1863). The source of other DNA's which may be used will be apparent to those of skill in the art of respiratory disease.

It will be appreciated that when the cells to be transfected are cells in culture, whether they are macrophages, tumor cells, fibroblast cell cultures or any other cell type, the DNA which will be used to transfect the cells will depend upon the particular application desired.

The DNA molecule may be contained within a plasmid, or may simply comprise the sequences to be transfected and any additional nucleic acid sequences which render the DNA more stable, or which enhance expression of the desired gene. Thus, the DNA molecule may include other sequences which enhance the expression of the DNA in a cell in which it has been introduced. For example, the DNA molecule may include promoter sequences, as described herein, for expression of the product therefrom. In addition, the DNA molecule may include an origin of DNA replication which confers on the DNA the ability to replicate in the cell in which it has been introduced. Such origins of DNA replication are preferably eukaryotic replication origins and include any origin of DNA replication which facilitate replication of the DNA in a cell. Eukaryotic origins of DNA replication include, but are not limited to, the Epstein Barr virus DNA replication origin and associated DNA elements for facilitating replication, and the SV40 origin of replication. The ligation of an origin of DNA replication to a desired DNA molecule is well known in the art and is described, for example, in Sambrook et al. (1989, Molecular Cloning: A Laboratory Manual, Cold Spring Harbor, N.Y.). DNA which comprises an origin of DNA replication is useful in that it may have a longer therapeutic effect in an animal to which it is administered than DNA which does not comprise such an origin.

The DNA molecule to be transfected into cells, whether or not it is accompanied by additional sequences, is referred to herein as "an isolated nucleic acid molecule." It will be appreciated that as technology for the isolation of and modification of RNA advances, it may be possible to used an RNA molecule in place of the DNA molecule described herein. Thus, the term "isolated nucleic acid" should be construed to encompass both DNA and RNA.

By "isolated nucleic acid" as used herein is meant a nucleic acid sequence, a DNA or and RNA sequence, which has been separated from the sequences which flank it in a naturally occurring state, e.g., a DNA or RNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state. The term therefore includes, for example, a recombinant DNA which is incorporated into a vector or into an autonomously replicating plasmid, or as a cDNA or a genomic or cDNA fragment produced by PCR or restriction enzyme digestion, independent of other sequences. It also includes a recombinant DNA which is part of a hybrid gene encoding additional polypeptide sequence and optionally having promoter/regulatory sequences fused thereto to enhance or control expression of a protein encoded thereby.

The isolated nucleic acid should be construed to include a DNA or RNA sequence specifying the desired DNA or RNA, and any modified forms thereof, including modifications of the DNA or RNA which render the nucleotide sequence more stable when it is cell free or when it is associated with a cell. Modifications of nucleic acids may also be used to enhance the efficiency with which a nucleic sequence is taken up by a cell or the efficiency with which it is expressed in a cell. Any and all combinations of modifications of the nucleotide sequences are contemplated in the present invention.

The invention should not be construed as being limited solely to DNA or RNA encoding the aforementioned genes. Once armed with the present invention, it is readily apparent to one skilled in the art that DNA or RNA molecules which are homologous to the aforementioned genes and which encode proteins or peptides which are substantially similar in function to the function of the proteins encoded by the aforementioned genes may be obtained by following the well known procedures described in the art for the isolation of DNA or RNA molecules which are homologous to known DNA or RNA molecules.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

By the term "substantially homologous" as used herein, is meant DNA or RNA which is about 50% homologous, more preferably about 70% homologous, even more preferably about 80% homologous and most preferably about 90% homologous to the desired nucleic acid. Genes which are homologous to the desired gene should be construed to be included in the invention provided they encode a protein or polypeptide having a biological activity substantially similar to that of the desired gene.

The desired nucleic acid useful in the invention is nucleic acid encoding a gene which when administered to a mammal, preferably, a human, serves to alleviate the symptoms of or serves to cure a respiratory disease in the mammal. The preferred diseases to be treated include cystic fibrosis, asthma, emphysema, idiopathic pulmonary fibrosis and congenital surfactant deficiency. The preferred DNAs to be used therefore include the CFTR gene, an asthma gene, the α1AT gene, a gene affecting idiopathic pulmonary fibrosis and the SP-B and SB-C genes. The invention should also be construed to include biologically active fragments of each of these genes and should further be construed to include all forms of DNA, including cDNA, genomic DNA and synthetic DNA.

By the term "biologically active," as used herein, is meant a fragment of DNA which encodes a polypeptide that retains the biological activity of the full length protein from which the polypeptide is derived.

Using CFTR as an example, but understanding that the invention is not limited thereto, biologically active fragments of an isolated nucleic acid encoding CFTR will ordinarily be at least about 240 contiguous nucleic acids in length, typically at least about 500 contiguous nucleic acids, more typically at least about 1000 continuous nucleic acids, and even more typically, at least about 4000 to about 6000 contiguous nucleic acids in length. A fragment of nucleic acid encoding CFTR must be biologically active in order to be useful in the methods of the invention. The biological activity of CFTR is defined as an increase in efflux of chloride ions in epithelial cells following stimulation of the cells with either forskolin or cyclic AMP. In addition to the measurement of chloride ion efflux, CFTR activity may also be identified by measuring iodine efflux or efflux of other halogens in cells, wherein an increase in efflux of the halogen in cells treated with the putative CFTR gene fragment, which cells are also stimulated by either forskolin or cyclic AMP, identifies the fragment as a biologically active fragment of the CFTR gene.

Also contemplated in the invention is the transfection of cells either in vivo or in vitro with a DNA molecule which is in the antisense orientation with respect to the coding strand of double stranded DNA. Thus, the invention also includes an isolated nucleic acid having a nucleotide sequence which is in the antisense orientation (i.e., is complementary) to a portion or all of a nucleic acid encoding a gene, the expression of which is detrimental to a host or cell.

During the development of certain respiratory diseases in a human, genes are expressed, which if inhibited, would serve to arrest the development of the disease. Such genes are referred to herein as genes which are required for the development of the respiratory disease. For example, during the development of asthma in a human, cytokines such as IL-4 and IL-5, and leukotrienes are expressed which facilitate the development of an asthma attack. Inhibition of expression of the genes encoding these products would serve to arrest the development of the asthma attack. The invention therefore contemplates the use of DNA molecules which are in the antisense orientation to genes encoding products which are required for the development of a respiratory disease.

By "complementary" to all or a portion of a gene, as used herein, is meant a sequence of nucleic acid which does not encode the protein specified by the gene. Rather, the sequence which is being expressed in the cells is identical to the non-coding strand of the subject gene and thus, does not encode the protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The antisense nucleic acids which are useful in the present invention include those which have been modified to enhance their stability or otherwise enhance their ability to inhibit gene expression. Antisense nucleic acids which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No: 5,034,506) or polyamide backbone structures (Nielsen et al., 1991, Science 254: 1497) may also be used. The examples of antisense oligonucleotide modifications described herein are not exhaustive and it is understood that the invention includes additional modifications of the oligonucleotides of the invention which modifications serve to enhance the therapeutic properties of the oligonucleotide without appreciable alteration of the basic sequence of the oligonucleotide.

Methods of preparing the oligonucleotides used in accordance with this invention are routine in the art, for example, solid phase synthesis is a well known technique commonly used to synthesize such oligonucleotides. It is also well known to use similar techniques to prepare other oligonucleotides such as phosphorothioate and alkylated derivatives.

The invention should thus be construed to include nucleic acid encoding desired proteins and fragments of nucleic acid encoding desired polypeptides; and, nucleic acids and fragments of nucleic acids which are in the antisense orientation to nucleic acid encoding the desired protein or polypeptide.

By the term "transfection" as used herein, is meant the transport of nucleic acid into a cell and the expression of the nucleic acid therein.

The term "expression of a nucleic acid" as used herein means the synthesis of the protein product encoded by the nucleic acid.

A suitable transfection mixture for transfer of nucleic acid into airway epithelial cells comprises any ordinary transfection mixture available in the art, including, but not limited to, isotonic medium, for example, DMEM, which is preferably serum-free. In addition, other compounds may be added to the transfection mixture for the purpose of improving the stability of the complex and/or improving the transfection efficiency in the desired cells. Such compounds include, but are not limited to, chloroquine, glycerol and fusogenic peptides. It will be appreciated that the amount of such compounds to be added to the transfection mixture will vary depending on any number of factors, including, but not limited to, the type of compound being used, whether transfection is conducted in vitro or in vivo, the size of the nucleic acid to be transfected and the amount and relative ratios of the nucleic acid to substituted polylysine. Examples of the use of such enhancing compounds are included herein in the experimental details section.

For transfection in vitro, the nucleic acid encoding the gene to be expressed and glycosylated polylysine are added to cells in the appropriate transfection mixture. The cells are incubated for a period of time, generally about three to about four hours, and the cells are then washed, growth medium is added and the cells are incubated for an additional about twenty four to about seventy two hours. Expression of the gene is assessed using any number of detection methods for the production of protein, including, but not limited to immunological protein detection methods, such as Western blotting, immunofluorescence, ELISA, and the like. When the nucleic acid to be transfected is CFTR DNA, expression of CFTR nucleic acid is assessed using any of the aforementioned techniques including in situ hybridization and, in addition, expression is measured in any CFTR assay such as the assays described herein in the experimental details section.

For transfection of cells in vivo, a plasmid or other DNA molecule encoding the desired protein is complexed with glycosylated polylysine and the complex is administered to an animal following the procedures described herein for transfer of reporter plasmids to animal airway epithelial cells. Expression of the protein is assessed as described herein. Administration of lactose substituted polylysine/DNA complex to airway epithelial cells of animals may be accomplished by aerosol through the nasal passages, by bronchoscopy or by any other method available in the art, such as by tracheal catheter.

Using CFTR as an example, but appreciating that the invention is not limited solely to the use of CFTR, procedures for transfection of cells in vivo are now described. In addition to mice, rabbits and other vertebrate animals may be used, including non-human primate animals, to examine the introduction of DNA, for example, CFTR into the airway epithelial cells of these animals using the methods described herein.

To test the effectiveness of, for example, CFTR added to airway epithelial cells in vivo, the tracheal xenograft model may be used (Engelhard et al., 1992, *J. Clin. Invest.* 90:2598–2607). This model is described in detail herein in the experimental details section. Essentially, the model comprises an immunodeficient mouse having a denuded rat-trachea transplant positioned under the skin on which CF airway epithelial cells are grafted. CFTR nucleic acid complex with glycosylated polylysine suspended in a suitable transfection mixture is administered to the animals at the site of the xenograft. After a period of time, generally about four hours, the mixture is removed. Correction of the CF-associated defect is then assessed by measuring transepithelial potential difference with amiloride stimulation after about thirty six to about forty hours post transfection.

Alternatively, other animals may also be used for administration of CFTR using glycosylated polylysine. Such animal models include, but are not limited to, adult mice and rabbits (Lisby et al., 1996, *Pediatr. Res.* 39: 389A) and non-human primates (Simon et al., 1993, *Human Gene Therapy* 4:771–780. Transgenic animal models may also be useful in the invention.

According to the methods of the invention, glycosylated polylysine complexed to CFTR DNA may be administered to a human having CF in a manner similar to that described for the animal models discussed herein. Essentially, the human is anesthetized unless the DNA is to be administered via an aerosol nebulizer, and the DNA/polylysine complex is administered by bronchoscopy, or by using a tracheal catheter, at doses of about 500 $\mu$g to about 10 mg of DNA and an appropriate amount of glycosylated polylysine in a volume of about 1 ml to about 100 ml depending on the age and size of the individual and the severity of the disease. Typically, a normal adult will receive about 50 ml of a DNA solution having about 5 mg of CFTR DNA. The administration of a compound to a human by aerosol, bronchoscopy, or tracheal catheter, is well known in the art and is described, for example, in Curiel et al. (1996, *Am. J. Respir. Cell MoL Biol.* 14:1–18). It will be appreciated that the precise method of administration of nucleic acid complexed with glycosylated polylysine to a human will depend on any number of factors including the age of the individual and the severity of the disease. The precise mode of treatment of a human will be apparent to the artisan skilled in the treatment of CF and will be tailored by the artisan to the individual being treated.

The DNA/polylysine complex is administered to the human about once a month or less, or about once every two months, or even about once every three months. The treatment regime to be used will depend on several factors including the age of the individual, the extent of the CF symptoms and the overall health of the individual, the length of time since the onset of symptoms, etc.

The invention should also be construed to include treatment of disease in utero using glycosylated polylysine DNA complexes. Again, using CFTR as an example, given the availability of genetic tests capable of identifying a defective CFTR gene, it is now possible to determine whether a fetus in utero has a defective CFTR gene. Such defects can be corrected in utero, prior to the onset of symptoms following birth, thereby preventing many of the sequelae of CF experienced by children and young adults with this disease. Treatment in utero is accomplished by following the procedure described in Sekhon et al. (1995, *Nature Med*.1:1201–1203).

Pharmaceutical compositions suitable for administration of glycosylated polylysine nucleic acid complexes to the airway epithelial cells of an animal in vivo include, but are not limited to, any of the compositions described herein for transfection of cells in culture.

Also encompassed by the invention is a method of identifying a compound capable of modulating the activity of CFTR. For example, cells in culture which are transfected with the CFTR gene may be used to identify a compound which has an affect on CFTR activity. Thus, cells which are transfected with the CFTR gene provide an in vitro system for the identification of compounds which modulate CFTR activity. To practice this aspect of the invention, transfected cells expressing CFTR may be treated with a compound which is predicted to affect CFTR activity, and the affect of the compound on CFTR activity may be assessed by using any of the procedures described herein. In this manner, compounds having an effect on CFTR activity are identified and can be further tested for their capability as therapeutic agents for treatment of CF, also as described herein.

The manner in which a compound capable of modulating CFTR activity is identified is straightforward and simple to practice one armed with the teaching described herein. For this reason, the invention should be construed to include any and all compounds which are identified following the methods described herein.

Also included in the invention is a kit comprising an isolated nucleic acid comprising a DNA useful for treating a human, for example, but not limited to CFTR, or a biologically active fragment thereof, a glycosylated polylysine and instructions for using the kit. Optionally, the kit may include one or more of glycerol, fusogenic peptide or chloroquine. The kit is useful for transfection of airway epithelial cells, useful, for example, for the identification of compounds capable of modulating CFTR activity, and is also useful for treatment of humans having CF. The instructions for using the kit therefore depend on the procedure for which the kit is to be used.

In the case of cell transfection in vitro, the instructions comprise directions on how to mix the desired nucleic acid and polylysine to the appropriate proportions, how to treat cells prior to, during and following addition of the transfection mixture to the cells, and how to assess CFTR activity in CFTR transfected cells. These instructions simply embody the examples provided herein.

In the case of administration of isolated CFTR nucleic acid complexed with glycosylated polylysine to a human, the kit may also comprise a nebulizer into which the transfection mixture is placed. Thus, in this case, instructions for using the kit comprise directions for mixing the isolated nucleic acid and glycosylated polylysine, and directions including dosages, as described herein, for administering the complex to a human. Such administration directions may also include instructions as to the amount of transfection mixture to be added to the nebulizer and the manner in which the nebulizer is to be used on the patient. Such instructions and directions will depend on factors such as the age of the individual and the severity of the disease, but in any event, will be apparent to the artisan skilled in the treatment of CF.

The invention should not be construed to be limited to transfection of cells in vivo in an animal for the purpose of treatment of a disease. Rather, the invention should also be construed to include transfection of a variety of cells in vitro using glycosylated polylysine as a delivery vehicle. Currently available technology for delivery of DNA to cells in vitro is limited with respect to the efficiency with which the DNA is delivered. This is particularly true in the case of cells which are considered to be difficult to transfect, such as monocytes and macrophages, for example. Several commercially available cell transfection kits include a range of lipid compositions which can be mixed with a reporter DNA for transfection into a variety of cell types. The reporter DNA typically comprises a gene encoding a detectable protein product operably linked to a promoter/enhancer sequence for driving expression of the reporter gene when transfected into cells. The lipid composition which effects the most efficient transfection of reporter DNA into a given cell type is then selected as the composition of choice for transfection of other genes into that particular cell type. One example of such a cell transfection kit is Perfect Lipid™.

Thus, according to the invention, a kit is provided which comprises a selection of glycosylated polylysine derivatives and optionally includes at least one type of reporter DNA molecule. The selection of polylysine derivatives includes polylysine substituted with lactose, α-glucose, β-galactose, mannose, mannose-6-phosphate, fucose and N-acetylglucosamine. The amount of each polylysine derivative to be used for transfection of cells will vary depending on any number of factors including the type of DNA and type of cells to be transfected. Typically, the ratio of polylysine derivative to DNA will be from about 1:1 to about 1:15.

By the term "a selection of polylysine derivatives," as used herein, is meant a combination of polylysine derivatives, each one of which is packaged individually so that they are not mixed together.

Reporter DNAs which can be optionally included in the kit include, but are not limited to plasmids or other forms of DNA comprising genes which encode chloramphenicol acetyl transferase, luciferase, green fluorescent protein gene, β-galactosidase, and the like. Essentially, a reporter DNA includes any DNA encoding a product which is detectable in transfected cells. The reporter DNA also comprises a promoter/regulatory sequence for driving expression of the DNA in a cell in which the DNA is transfected. Such promoter/regulatory sequences include, but are not limited to, constitutive promoter/regulatory sequences, such as, but not limited to the SV40 early promoter, the cytomegalovirus immediate early promoter and the Rous sarcoma virus promoter/enhancer, tissue specific promoter/regulatory sequences and inducible promoter sequences. The type of reporter gene and the promoter sequence to which it is operably linked will depend on the type of cells to be transfected and will be readily apparent to one of skill in the art of cell transfection and gene expression. Typically, the concentration of DNA used in a transfection assay will be about 1 μg to about 40 μg of plasmid mixed in the desired ratio with the glycosylated polylysine.

Also optionally included in the kit are compounds which further enhance the transfection of glycosylated polylysine DNA complexes into cells. Such compounds include glycerol which may be used at a preferred concentration of about 5%, although the use of glycerol at concentrations other than 5% is also contemplated, for example, glycerol concentrations of about 1% to about 8% are contemplated.

In addition, it has been discovered in the present invention that fusogenic peptides may be used to enhance the transfection efficiency of glycosylated polysine DNA complexes into cells. Examples of fusogenic peptides which may be included in the cell transfection kit are provided in the experimental details section herein, and include, but are not limited to, E5CA-GLFEAIAEFIEGGWEGLIEGCA [SEQ ID NO:1] (Midoux et al., 1993, Nucleic Acids Res. 21:871–878), HA-2-GLFEAIAGFIENGWEGMIDGGGC [SEQ ID NO:2] (Wagner et al. 1992, Proc. Natl. Acad. Sci. USA 89:7934–7938) and JTS-1-GLFEALLELLESLWELLLEA [SEQ ID NO:3] (Gottshalk et al., 1996, Gene Ther. 3:448–457). While the peptides may be used in the transfection mixture at a preferred concentration of about 10 μg, other concentrations of fisogenic peptide may also be used. The concentration of fusogenic peptide useful in the methods of the present invention may vary from about 1 μg to about 50 μg.

In addition, the kit may further include an amount of chloroquine, preferably to be used at a concentration of about 100 μM, although other concentrations of chloroquine are also contemplated. The concentration of chloroquine which may be used may vary from about 30 μM to about 150 μM.

As described herein, DNA complexed with lactosylated polylysine may be transfected into either immortalized or primary cultures of airway epithelial cells with high efficiency. While not wishing to be bound by any theory, it is believed that transfection of these cells by lactosylated polylysine DNA complexes occurs via receptor mediated endocytosis. Since many other cell types also have the capacity for receptor mediated endocytosis, a kit comprising a variety of glycosylated polylysine derivatives for complexing to DNA will enable the transfection of a number of different cell types. Use of the kit will also enable the selection of a glycosylated polylysine derivative which effects high efficiency transfection of a particular cell type.

Taking alveolar macrophages as an example and bearing in mind that the use of the kit is in no way limited to this cell type, the kit may be used as follows. Each glycosylated polylysine derivative is individually complexed to a reporter DNA following the procedures described herein. Aliquots of cells are transfected with each complex and expression of the reporter DNA is assessed at selected times post transfection as a measure of transfection efficiency. The glycosylated polylysine derivative yielding the highest efficiency of transfection of the cells will be evident from the levels of expression of the reporter gene in each of the groups of transfected cells. This particular glycosylated polylysine derivative may then be used for all subsequent transfection experiments involving alveolar macrophages. In this way, it is possible to identify a means for high efficiency transfection of any number of different cell types using the kit of the invention.

The unique features of the cell transfection kit of the invention take advantage of the sugar dependent, receptor mediated endocytosis by chemical conjugation of sugars with polylysine which serves to reduce the positive charge of the polylysine while still permitting effective binding with a desired DNA, all DNA's having an overall negative charge which charge facilitates binding of the DNA to compounds such as polylysine. The effectiveness of the method is augmented by the addition of adding glycerol and other known lysosomotrophic agents such as chloroquine and fusogenic peptides.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The results of the experiments described below are now summarized. When gluconoylated polylysine was used as a vehicle, the reporter plasmid pCMVLuc, comprising luciferase coding sequences under the control of the human cytomegalovirus (CMV) promoter/regulatory region, yielded a high level of expression of luciferase when transfected into immortalized CF/T43 cells. Luciferase activity in these cells was enhanced by 75-fold when the transfection mixture included 100 μM chloroquine. Luciferase gene expression persisted at high levels for up to at least 120 hours following transfection.

Glycosylated polylysinelpCMVLuc complexes were compared with the gluconoylated polylysine/pCMVLuc complex in immortalized airway epithelial cells. In some cases, pCMVLacZ encoding β-galactosidase was used (Gao et al., 1993, *Human Gene Therapy* 4:17–24). It was found that β-galactose, α-glucose and lactose-substituted polylysines resulted in 320%, 300% and 290% correspondingly higher levels of expression of the reporter gene luciferase than that expressed from gluconoylated polylysine complexed with the same DNA. The amount of luciferase expressed following transfection with the test polylysines ranged from 35 to 2 ng of luciferase per mg of cell protein in the following order: β-Gal=α-Glc=Lac>α-Gal=Rha= Man>β-GalNAc>α-GalNAc=α-Fuc. These results establish that the transfection efficiency of the subject cells is sugar dependent. Importantly, when primary cultures of either CF or non-CF airway epithelial cells grown from tracheal tissue explants were used, lactosylated polylysine yielded uniformly high expression of luciferase activity.

Materials Used in the Studies Described Herein

Lysis and assay buffers for determination of luciferase activity were obtained from Promega Corp. Luciferase was obtained from Boeringher-Mannheim Corp. Chloroquine was obtained from Sigma Chemical Co. The media used for cell culture included KGM obtained from Clonetics Corp., LHC-9 obtained from Biofluids Inc., and DMEM obtained from Hazelton Laboratories. Fetal bovine serum was obtained from Biofluids Inc.

Expression plasmids encoding the firefly luminescence gene were pSV2Luc (5 kb) (Brasier et al., 1989, *Biotechniques* 7:1116–1123), and pCMVLuc, having 6.2 kb (Erbacher et al., 1995, supra).

The plasmid pSV2Luc comprises the luciferase gene placed under the control of the SV40 early promoter, while pCMVLuc comprises the luciferase gene placed under the control of the human CMV promoter. When specified, pUT 650 containing a CMV promoter with Luc::Sh ble fusion gene (purchased from CAYLA) was used. Thus, the plasmids pCMVLuc and pUT 650 each contain the luciferase gene placed under the control of the human CMV promoter.

Preparation of Gluconoylated Polylysine

Polylysine, HBr (average molecular weight of 40,000; DP-190) obtained from Bachem Feinchemikalien, Bubendorf, Switzerland, was dissolved in $H_2O$ (1 g in 200 ml) and passed through an anion exchange column (Dowex 2×8, OH⁻ form, 20–50 mesh, 35×2.5 cm) in order to remove bromide ions (Derrien et al., 1989, *Glycoconjugate J.* 6:241–255). The effluent solution was neutralized with 10%p-toluene sulfonic acid in water (a non-cytotoxic compound) and was subsequently lyophilized.

Polylysine was partially substituted with gluconoyl residues as described (Derrien et al., supra). Briefly, δ-gluconolactone (15 mg; Aldrich Chemical Co.) was added to polylysine p-toluene sulfonate salt (50 mg) in 3 ml dimethylsulfoxide in the presence of 37 μl diisopropylethylamine (Aldrich Chemical Co.); the concentration was adjusted to 1% with water and the solution was stirred for 24 hours at 20° C. Gluconoylated polylysine was precipitated by adding 10 volumes of isopropanol and the precipitate was collected by centrifugation at 1800×g for 15 minutes. The pellet was washed with isopropanol, collected again by centrifugation, solubilized in distilled water and was lyophilized. The average number of GlcA residues bound per polylysine molecule was determined by $^1$H-NMR spectroscopy (300 MHZ, D20) and was found to be 74 residues.

Preparation of Glycosylated Polylysine Conjugates

Polylysine (DP 190) was partially substituted with sugar residues as described (Midoux et al., 1993, supra; Erbacher et al., 1995, supra). The 4-isothiocyanatophenyl-derivatives of either β-D-Gal, α-D-Gal, α-D-Glc, α-L-Rha, a-L-Fuc, α-D-Man, β-D-GlcNAc, α-D-GalNAc, β-D-GalNAc or β-D-Lac (Monsigny et al., 1984, *Biol. Cell* 51:187–196) were added to polylysinep-toluene sulfonate salt in dimethylsulfoxide in the presence of diisopropylethylamine and the mixture was incubated for 24 hours at 20° C. Glycosylated polylysine was precipitated and processed as described above for gluconoylated polylysine. The average number of sugar residues bound per polylysine molecule was calculated from the sugar content determined by the resorcinol sulfuric acid micromethod (Monsigny et al., 1988, *Biochimie* 70:1633–1649). The 66 lactose residues which bound to polylysine corresponded to a substitution of 35% of the amino groups of the molecule. The number of monosaccharide residues (77±10) which bound corresponded to a substitution of 41±5% of the amino groups of polylysine.

Figure 14:
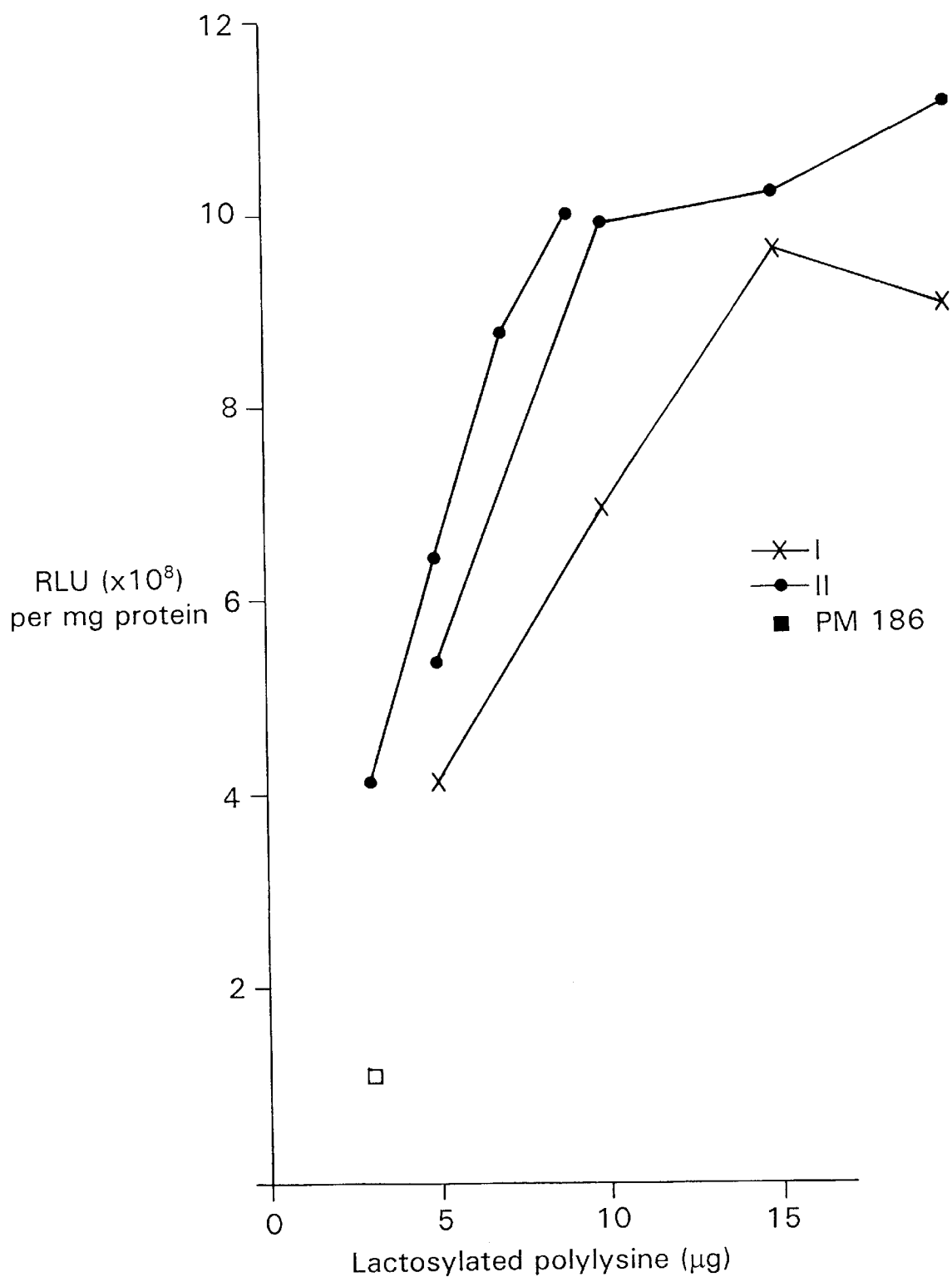
FIG. 14 is a graph depicting the enhancement of reporter gene expression in CF/T43 cells transfected with pCMVLuc coupled to different concentrations of several preparations of lactosylated polylysines. PM 186 is presented as the mean value 1.08±0.02 RLU (×$10^8$; n=10).

Modification of the above-described procedure yields a compound having even higher activity when complexed to pCMVLuc (FIG. 14). These modifications include beginning with 50% less starting material, mixing for 24 hours at 24° C., and washing the precipitate with isopropanol prior to lyophilization. About 20% of the amino groups on the polylysine are substituted with a glycosyl residue following this procedure.

In addition, glycosylated polylysines may be prepared by reductive complexing of lactose to polylysine with cyanoborohydride as described (Matrinez-Fong et al., 1994, *Hepatology* 20:1602–1608).

Cell Culture

The immortalized airway epithelial cell line, CF/T43 was obtained from a CF patient homozygous for the ΔF508 mutation. The cells were grown as described (Jetten et al., 1989, *Science* 244:1472–1475) in KGM medium.

Primary cultures of cells were prepared from tracheal explants or nasal polyps obtained from CF or non-CF patients at the time of surgery. Tracheal pieces were stripped and gently minced and were then placed in 25 cm² flasks coated with 25% fibronectin and incubated in LHC-9 medium at 37° C. in an atmosphere containing 5% $CO_2$. When epithelial cells grew out from the tissue, the pieces were removed to a new flask until additional epithelial cells grew out. This procedure was repeated several times. In some cases, the cells were obtained by protease treatment of the tissue as described (Wu et al., 1990, *Am. J. Respir. Cell Mol. Biol.* 3:467–478).

Prior to transfection, cells were seeded at $1.5 \times 10^5$ cells per 25 mm well in a 12-well plate (Corning). CF/T43 cells were then incubated for 24 hours at 37° C. and the primary cells were incubated from 24–48 hours at 37° C.

Transfection Procedures

The polymer/plasmid complexes were prepared as described (Erbacher et al., 1995, supra). Gluconoylated or glycosylated polylysine (20–30 μg of polylysine dissolved in 0.3 ml of serum-free DMEM) was added to the reporter plasmids (10 μg of DNA dissolved in 0.7 ml of serum-free DMEM) and the mixture was incubated for 30 minutes at ambient temperature unless otherwise specified. To prevent precipitation of the complex, the glycosylated polylysine was added to the plasmid at a rate of 15 μl per 30 seconds.

The lowest vehicle to DNA ratio (w/w) which exhibited complete retardation of all the DNA during electrophoresis was used. In that instance, all of the DNA was condensed and no free polymer was detected. The ratios were experimentally determined and ranged from 2 to 3. Next, 1 ml of DMEM containing the polymer/plasmid complex was supplemented with 1% heat inactivated fetal bovine serum and 100 μM chloroquine, and this mixture was added to each set of cells after removal of the growth medium from the cells.

After incubation at 37° C. for 4 hours unless otherwise specified, the transfection mixture was removed and the cells were further incubated at 37° C. in 2.0 ml KGM medium without additives. The cells were examined morphologically both after transfection and prior to lysis. Except when specified, all cells appeared normal. After 48 hours or at other time intervals, the cells were processed and expression of the transfected gene was assessed.

In order to increase the efficiency of transfection, the following protocol was adopted. Lactosylated polylysine (2 μg in 30 μl of DMEM) was added at a rate of 15 μl per 30 to 60 seconds to the appropriate plasmid (1 μg of plasmid dissolved in 70 μl DMEM). The mixture was allowed to sit for an additional 30 minutes at ambient temperature to form a complex. The complex so formed was supplemented as follows: 100 μM chloroquine and either 5% glycerol or 10 μg filsogenic peptide in the case of immortalized cells; and 5% glycerol with or without fusogenic peptide in the case of the primary cells. Each final mixture was contained in 1 ml of DMEM without serum and was then added to the cells. Thereafter, the transfection procedures was as described herein, and where noted, the cells were transfected daily for three days. The use of this protocol permits the use of larger quantities of vector/plasmid and this protocol is therefore useful for in vivo administration of DNA when it is necessary to maintain higher constant levels of expressed protein products.

To detect luciferase gene expression in transfected cells, the cells from each well were lysed by the addition of 100 μl of cell culture lysis reagent (25 mM Tris, pH 7.8; 2 mM EDTA; 2 mM DTT; 10% glycerol; 1% Triton X-100). The cell lysate was incubated for 15 minutes at ambient temperature and was transferred to Eppendorf tubes for centrifugation.

Measurement of Luciferase Activity

Luciferase activity was assessed by measuring luminescence following the method of De Wet et al. (1987, *Mol. Cell. Biol.* 7:725–737). The assay mixture (270 μM coenzyme A, 470 μM luciferin, 530 μM ATP, 20 mM tricine, 1.07 mM $(MgCO_3)_4$ $Mg(OH)_2$.$5H_2O$, 2.67 mM $MgSO_4$, 0.1 mM EDTA, 33.3 mM DTT, pH 7.8) was added at a ratio of cell lysate:assay mixture of 1:4, which was determined to be the optimum ratio for luciferase activity. Luminescence was recorded on a Luminat luminometer, LB 9501 (EG&G Berthold Analytical Instruments Inc.) for 5 sec and reported as relative light units (RLU). The luciferin/luciferase assay system was stable for more than 60 sec and duplicate wells were assayed in amounts of 5 to 20 μl to assure linearity of the results. Different experiments were performed and each was repeated twice. The standard assay points within experiments have a mean RLU of $3.7 \times 10^7 \pm 2.8 \times 10^6$ SEM (standard error of the mean) (n=11) and $1.3 \times 10^8 \pm 2.1 \times 10^7$ SEM (n=8) per mg of protein when gluconoylated or lactosylated polylysine, respectively, served as vehicle. A blank assay containing the cell extract but no plasmid, yielded a reading of 120–200 RLU. Protein concentration was determined using the method of Lowry et al, in cells which were lysed with 0.1 M NaOH or in the individual wells containing cells using the lysis buffer as background (Lowry et al., 1951, *J. Biol. Chem.* 193:265–275). The results are expressed as RLU per mg of protein. One picogram of luciferase is equivalent to 11,000 RLU under these assay conditions.

In experiments designed to measure the efficiency of gene expression, the plasmid pCMVLacZ may also be used, wherein gene expression is measured by measuring β-galactosidase activity using the chromogenic reagent X-gal.

Binding of FITC Neoglycoproteins

Bovine serum albumin (BSA) was lactosylated and subsequently labeled with fluorescein-conjugated isothiocyanate (FITC) as described (Monsigny et al., 1984, supra). CF/T43 cells (100–200 cells) were grown on cover slips for 2 days and after removal of the growth medium the cells were incubated with 20–100 μg per ml of either lactose-BSA-FITC or BSA-FITC at 4° C. for 30 minutes. In some cases, 0.1 or 0.2 M lactose was added with the neoglycoprotein to block binding. The coverslips were washed three times at 4° C. with phosphate buffered saline, pH 7.3, and fixed in methanol for 10 minutes at 4° C. After mounting with SlowFade™-light Antifade Kit (Molecular Probes Inc.), binding was assessed using a Nikon Diaphot 300 microscope.

The Use of Gluconoylated Polylysine as a Transfection Vehicle in CF/T43 Cells

To establish some optimum parameters for transfection of cells using glycosylated polylysines, gluconoylated polylysines were initially examined in the transfection assays described herein. Seventy-four amino groups of polylysine (DP 190) were substituted with gluconoyl residues by acylation with δ-gluconolactone. This substitution provided a partially neutralized derivative of polylysine which was highly water-soluble and an efficient vehicle for transfecting various cell lines (Midoux et al., WO 95/30020). Gluconoylated polylysine was an efficient vehicle for the transfer of several luciferase plasmids into CF/T43 cells, resulting in high levels of gene expression in these cells.

Two different luciferase encoding plasmids, wherein the luciferase was placed under the control of two different promoters (pCMVLuc or pSV2Luc) were used. Either of these plasmids was complexed to gluconoylated polylysine at a 2 to 1 (w/w) ratio of polylysine to DNA. The plasmid pCMVLuc was 26 times more effective than pSV2Luc for the expression of luciferase in CF/T43 cells. Controls included cells transfected with either of the plasmids or the vehicles on their own.

Optimal conditions for Gene Transfer Using Gluconoylated Polylysine

A series of experiments were performed to determine the optimum conditions for the expression of the luciferase gene following transfection of a luciferase encoding plasmid into CF/T43 cells.

To assess the effects of chloroquine on transfection, cells were transfected in the presence of increasing concentrations of this compound. The use of chloroquine in the transfection mixture resulted in an increase in the transfection efficiency of CF/T43 cells by the gluconoylated polylysine/plasmid complex in a concentration-dependent manner (FIG. 1). The amount of luciferase activity expressed in cells transfected with a chloroquine-containing mixture was 75-fold higher than in cells transfected in the absence of chloroquine. An approximately 26-fold increase in luciferase activity was observed when 100 μM chloroquine was used compared with the level of luciferase activity in cells transfected in the presence of 10 μM chloroquine. When 200 μM chloroquine was used the level of luciferase activity was significantly decreased in transfected cells. Fetal bovine serum, at a concentration of 1–10%, had little effect on the transfection efficiency during a 4 hour transfection time period. Thus, the concentration of chloroquine used affected the transfection efficiency and the highest level of reporter gene expression was observed at a chloroquine concentration of 100 μM.

Figure 2A:
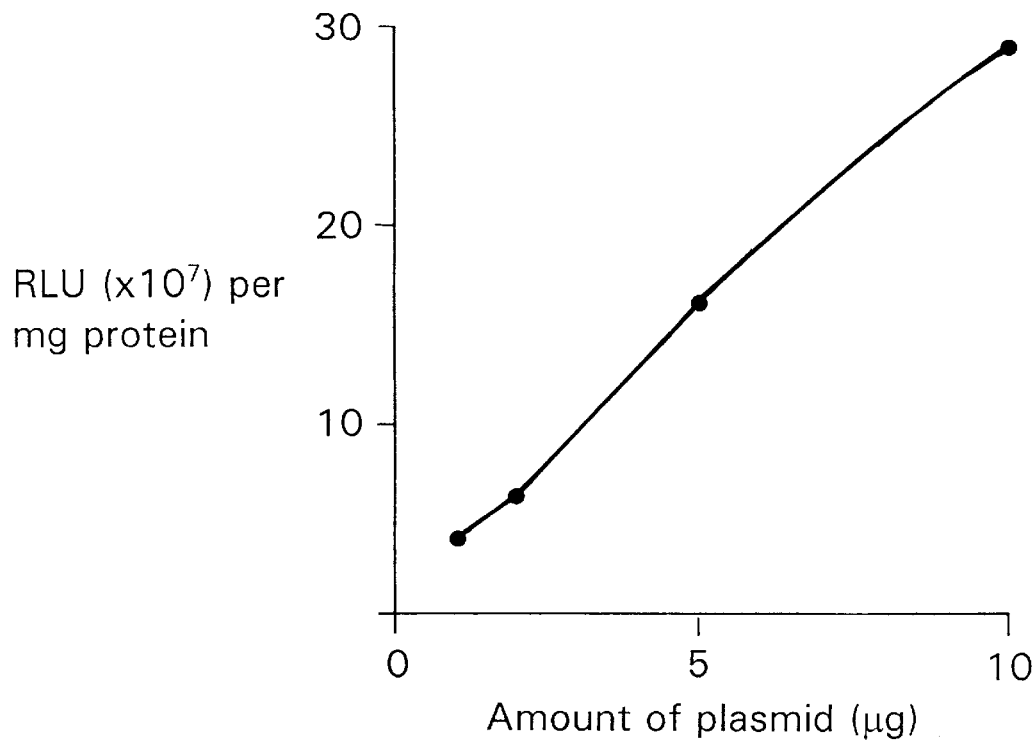
In FIG. 2A, a transfection assay was performed as described in FIG. 1 wherein the amount of gluconoylated polylysine:pUT 650 (2:1, weight/weight) was varied as indicated, in relationship to the cell number which was maintained at a constant value of $1.5 \times 10^5$ cells per culture well. When no plasmid was present in the mixture, a blank value was obtained.

To assess the effect of plasmid concentration on transfection efficiency and gene expression, the concentration of the plasmid pCMVLuc (pUT 650) was varied from 0.1 to 10 μg, while maintaining the gluconoylated polylysine:plasmid ratio at 2:1 (FIG. 2A). When the concentration of the plasmid complex was linearly increased, luciferase activity also increased linearly. A concentration of 1 μg of pCMVLuc was used in subsequent experiments, unless otherwise stated.

Increasing amounts of plasmid did not result in increased toxicity to cells because gluconoylated polylysine/plasmid complexes were designed to have the lowest possible molar ratio between the vehicle and DNA. In other words, the ratio of polylysine to DNA was adjusted so that the transfection medium did not contain any DNA-free vehicle which might otherwise contribute to cellular toxicity (Erbacher et al., 1995, supra). When the vehicle:plasmid ratio was 2:1 there were no observed morphological changes in the cells. When non-substituted polylysine was used as a vehicle complexed with pCMVLuc at a ratio of 2:1 (w/w), luciferase was expressed to a level of only 40% of that observed using gluconoylated polylysine.

Figure 2B:
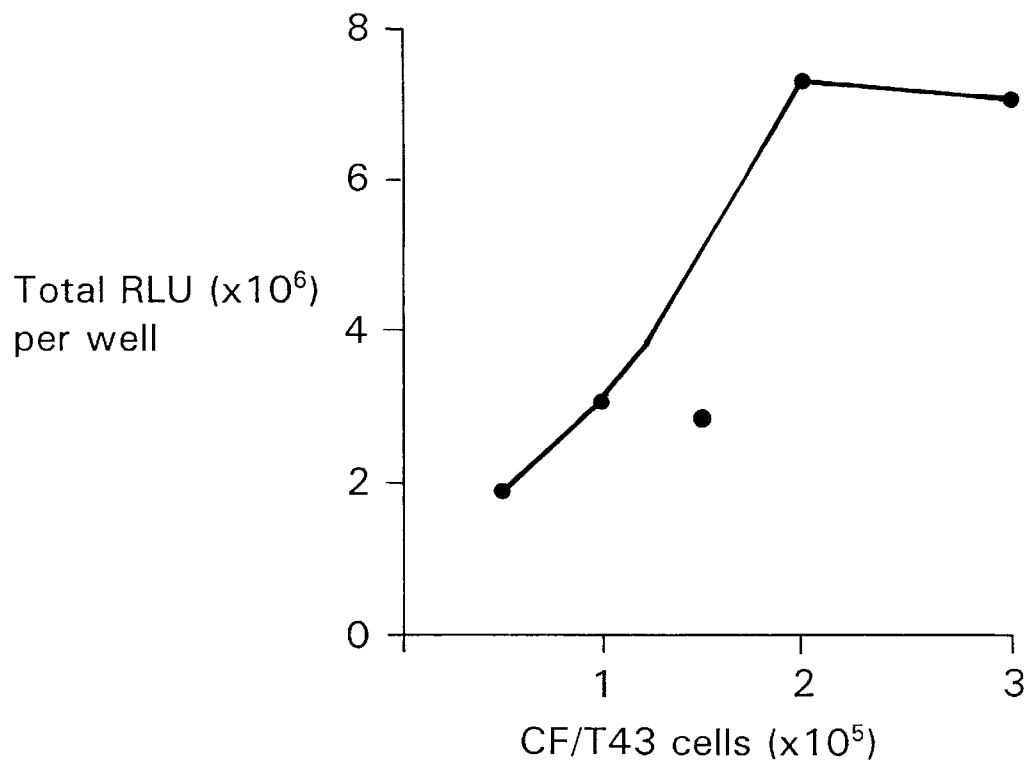
In FIG. 2B, a transfection assay was performed as described in FIG. 1, wherein a constant amount (1 $\mu$g) of the plasmid, pCMVLuc and gluconoylated polylysine (2 $\mu$g) was added to a varying number of CF/T43 cells per well as indicated in the figure.

To assess the effect of cell number on transfection efficiency and gene expression, the number of CF/T43 cells in each transfection assay was varied while maintaining the plasmid concentration at 1 μg and the ratio of gluconoylated polylysine to DNA at 2:1 (w/w). In the majority of the experiments, CF/T43 cells were seeded at a concentration of $1.5 \times 10^5$ cells per 25 mm well. However, when $2 \times 10^5$ cells per well were used, a higher level of luciferase activity was observed (FIG. 2B). When the cell concentration was increased to greater than $2 \times 10^5$ cells per well, no additional increase in luciferase activity was observed. Thus, the number of cells seeded in each well has an effect on the transfection efficiency of the cells.

Figure 3A:
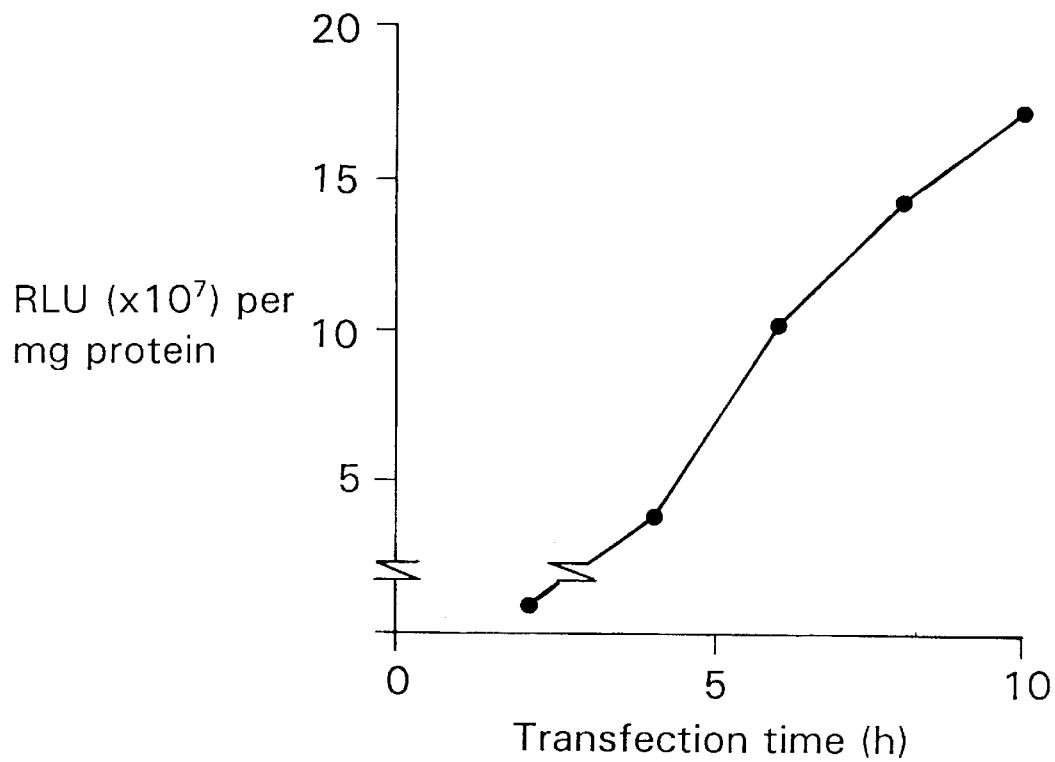
In FIG. 3A, the level of expression of the reporter gene, pUT 650, was assessed at various times post-transfection of CF/T43 cells. Chloroquine (100 $\mu$M) was included in the transfection mixture. The DNA complex was added to CF/T43 cells in the transfection medium and at various times the transfection mixture was removed and the cells were incubated in KGM medium for 48 hours. The amount of luciferase expressed in the cells was then measured. When cells were transfected for 2 hours, $8.5 \times 10^6$ RLU per mg of protein was detected.

The effect of the length of time of transfection on transfection efficiency and gene expression was assessed as follows. DNA was added to cells in a standard transfection mixture at a gluconoylated polylysine to DNA ratio of 2:1. Cells were incubated with the DNA transfection mixture for 4 to 10 hours in the presence of 100 μM chloroquine. At each time point tested, the transfection mixture was removed from the cells, the cells were washed and incubated in fresh medium for 48 hours prior to lysis and luciferase assay. From FIG. 3A it is evident that the amount of luciferase activity increased about 4-fold in transfected CF/T43 cells when the transfection time was increased from 4 to 10 hours. In another experiment using 5 μg of plasmid, luciferase activity was observed to peak a transfection time of 6 hours.

Figure 3B:
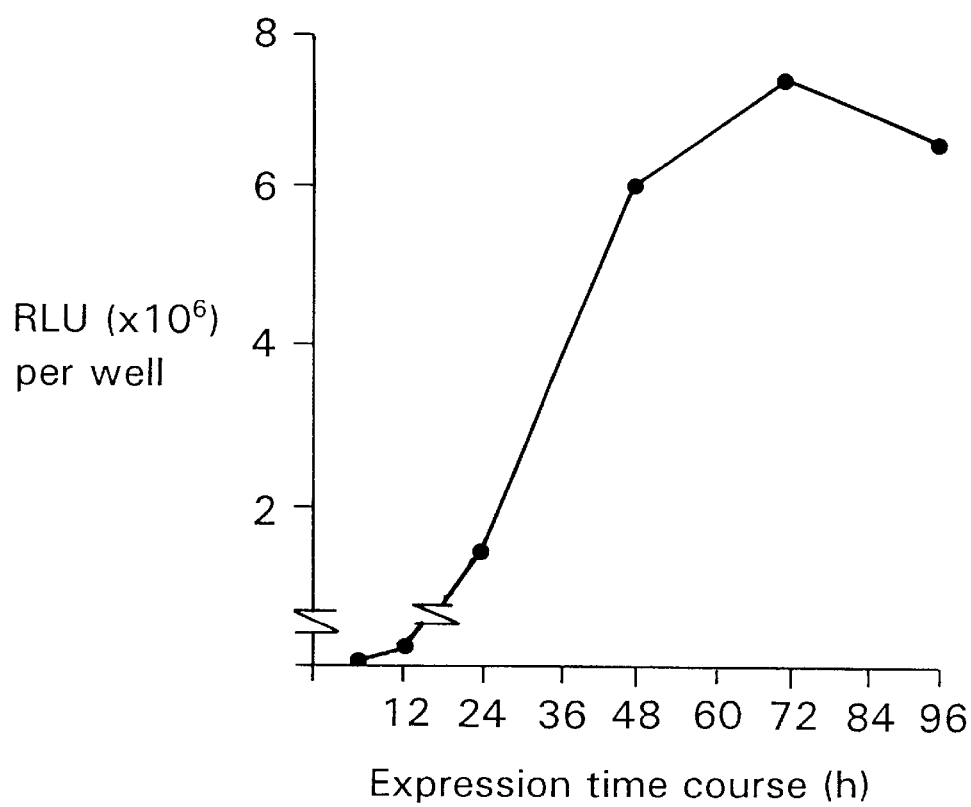
In FIG. 3B, CF/T43 cells were transfected for 4 hours with the plasmid pCMVLuc and gluconoylated polylysine. Following transfection, the cells were washed and were incubated in KGM medium for the times indicated on the figure. At those indicated times, the amount of luciferase expressed in the cells was assessed. At 6 and 12 hours following the 4 hour transfection period, $3 \times 10^4$ and $1.3 \times 10^5$ RLU, respectively, were detected per well.

To assess the effects of incubation time post transfection on gene expression in transfected cells, cells were transfected for 4 hours, and at various time post transfection, the cells were harvested and luciferase activity was measured (FIG. 3B). Maximal luciferase activity was observed between 48 and 96 hours post transfection. In fact, when the time was extended to 120 hours post transfection, a very high level of luciferase activity (130% of that observed at 48 hours post transfection) was observed. Since during the course of this latter experiment the cells were incubated in growth medium, the cell number actually increased, therefore apparently lowering the amount of luciferase activity when measured as activity per mg of protein.

The Use of Glycosylated Polylysines for Transfection of CF/T43 Cells

Glycosylated polylysines containing varying numbers of mono or disaccharides were prepared as described herein. Polylysine substituted with monosaccharides contained an average of 77±10 sugar residues corresponding to the substitution of 41±5% of the amino groups of polylysine (DP-190). Lactosylated polylysine contained an average of 66 lactose residues corresponding to the substitution of 34% of the amino groups.

Glycosylated polylysine/plasmid complexes were made having the lowest polymer to DNA ratio (2 or 2.5 μg polylysine substituted with monosaccharides per μg pCMVLuc and 3 μg lactosylated polylysine per μg pCMVLuc). At these concentrations and ratios the following was observed: (i) a complete retardation of all the DNA during electrophoresis; (ii) complexes which had a pH near 7.0; (iii) a complete association of glycosylated polylysine with the DNA; and iv) high efficiency gene transfer.

Figure 4:
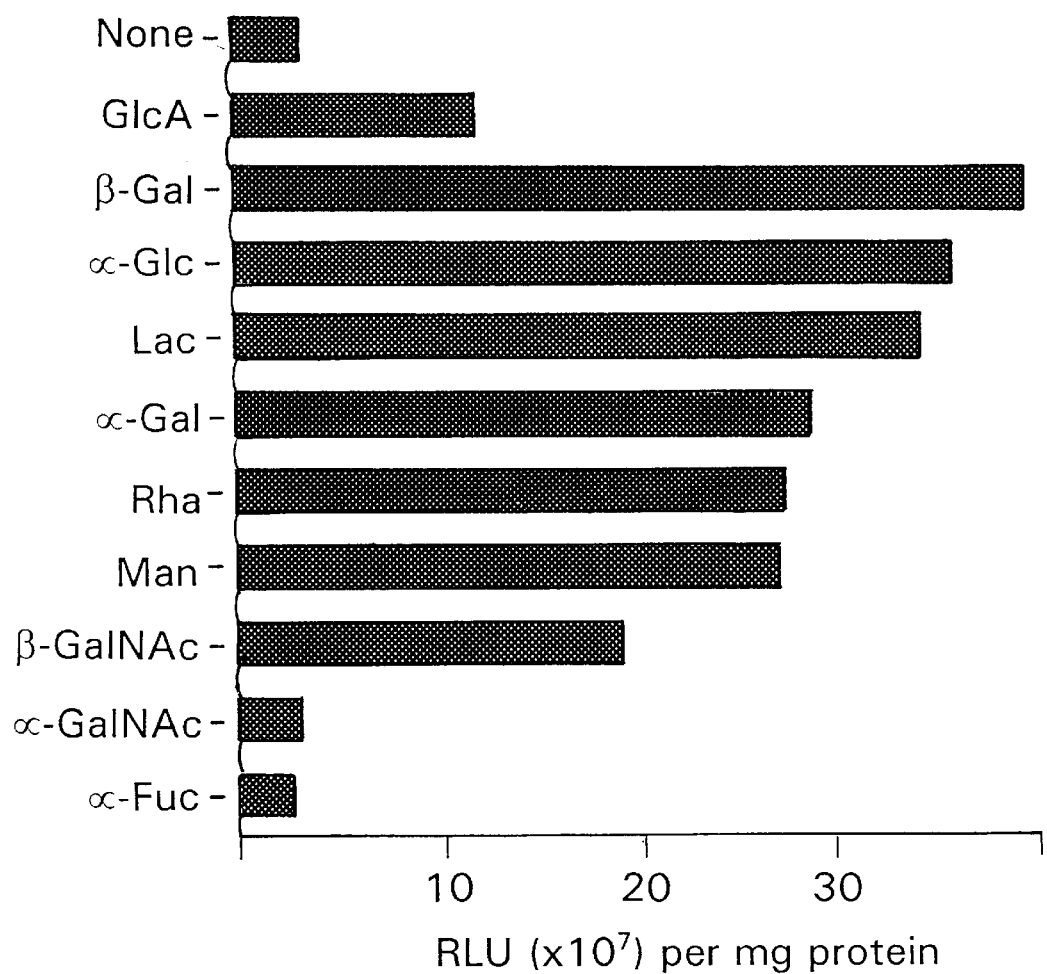
FIG. 4 is a graph depicting reporter gene expression in cells transfected with various glycosylated polylysines as vehicles. The substituted polylysines indicated on the figure were complexed with 5 $\mu$g of the reporter plasmid pCMV-Luc. CF/T43 cells were transfected for 4 hours, washed and incubated in KGM medium and luciferase activity was measured. "None" indicates that non substituted polylysine was added to the transfection mixture; "GlcA" is gluconoylated polylysine.

When transfection mixtures were prepared in this manner, the level of luciferase activity was observed to vary with the type carbohydrate contained on the polylysine (FIG. 4). The use of polylysine substituted with β-Gal, α-Glc or lactose complexed with pCMVLuc yielded luciferase activity at levels of 322%, 298% and 289%, respectively, when compared with the use of gluconoylated polylysine. Polylysine substituted with Rha, Man and α-Gal also yielded high expression of luciferase activity; however, several other carbohydrate substitutions, namely α-L-Fuc and α-GalNAc yielded negligible amounts of luciferase gene expression when used to transfect cells. The levels of luciferase activity ranged from 3.9 to $0.3 \times 10^8$ RLU/mg protein in the following order of polylysine complexes used in the transfection mixtures: β-Gal=α-Glc=Lac>α-Gal=Rha=Man>β-GalNAc>GlcA>α-GalNAc=α-Fuc.

In separate experiments, GlcNAc-substituted polylysine was not as efficient a vehicle as lactosylated polylysine; GlcNAc-substituted polylysine transfected cells exhibited less than 50% of the luciferase activity observed in cells transfected with lactosylated polylysine. Further, non-substituted polylysine was only 10% as effective as lactosylated polylysine in effecting expression of luciferase in transfected cells. Thus, α-glucose, β-galactose and lactose substituted polylysine are superior to other sugar substitutions on polylysine for transfer of DNA into immortalized airway epithelial cells.

Optimal Conditions for Lactosylated Polylysine Mediated Gene Transfer

The data presented in FIG. 4 establish that lactosylated polylysine is a highly efficient vehicle for the transfection of CF/T43 cells. To determine the optimal conditions for use of lactosylated polylysine as a transfection vehicle in CF/T43 cells, the following experiments were conducted.

Figure 5A:
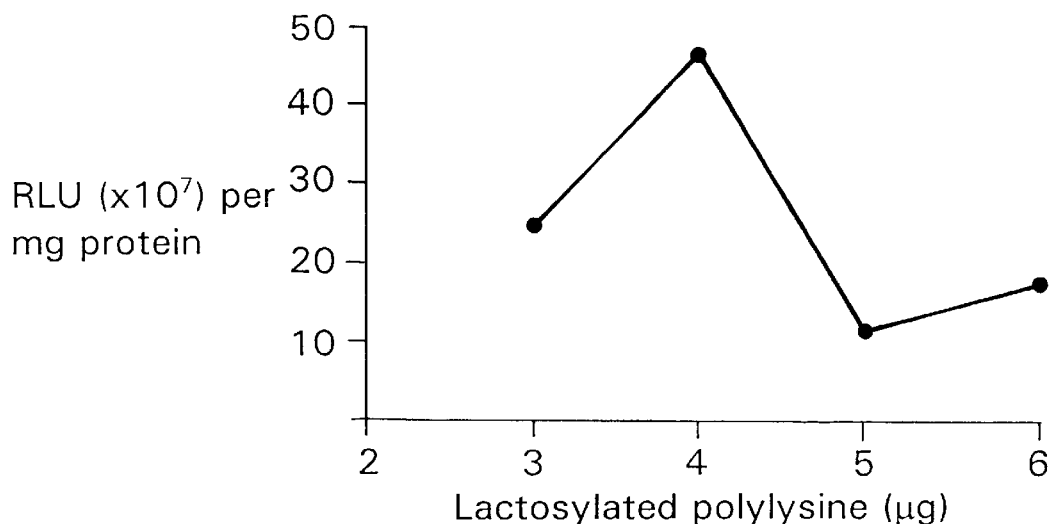
In FIG. 5A, one $\mu$g of pCMVLuc was used in the presence of 100 $\mu$M chloroquine while the concentration of lactosylated polylysine was varied as indicated.

The ratio (w/w) of the lactosylated polylysine to pCMV-Luc was varied to determine the optimum ratio for efficient transfection of plasmid. These results are shown in FIG. 5A. When a 4:1 ratio was used in the transfection mixture, the expression of luciferase in transfected cells was increased two-fold, compared with a 3:1 ratio.

Figure 5B:
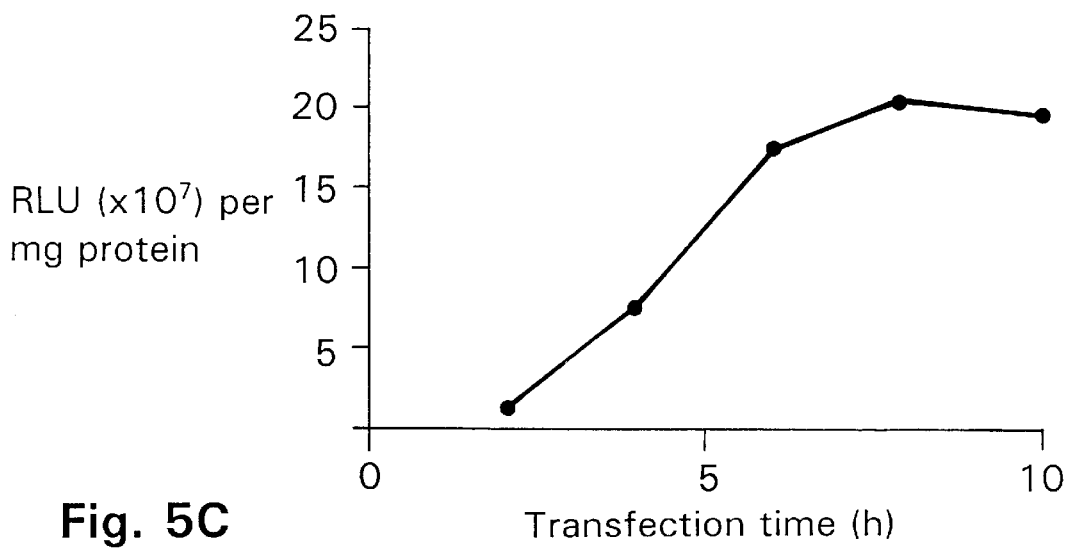
In FIG. 5B, the time of the actual transfection was varied from 2 to 10 hours using 3 $\mu$g lactosylated polylysine and 1 $\mu$g of reporter gene pUT 650 (i.e., in a w/w ratio of 3:1) in the presence of 100 $\mu$M chloroquine.

The effect of time on transfection efficiency was also determined. When the time of transfection was increased to 8 hours from 4 hours, luciferase activity was increased in transfected CF/T43 cells (FIG. 5B). However, at a transfection time of 8 hours, some morphological changes were observed in the cells. The optimal time of transfection using lactosylated polylysine in the presence of 100 μM chloroquine was approximately 6 hours. In these cells, expression of luciferase continued for up to 120 hours.

Figure 5C:
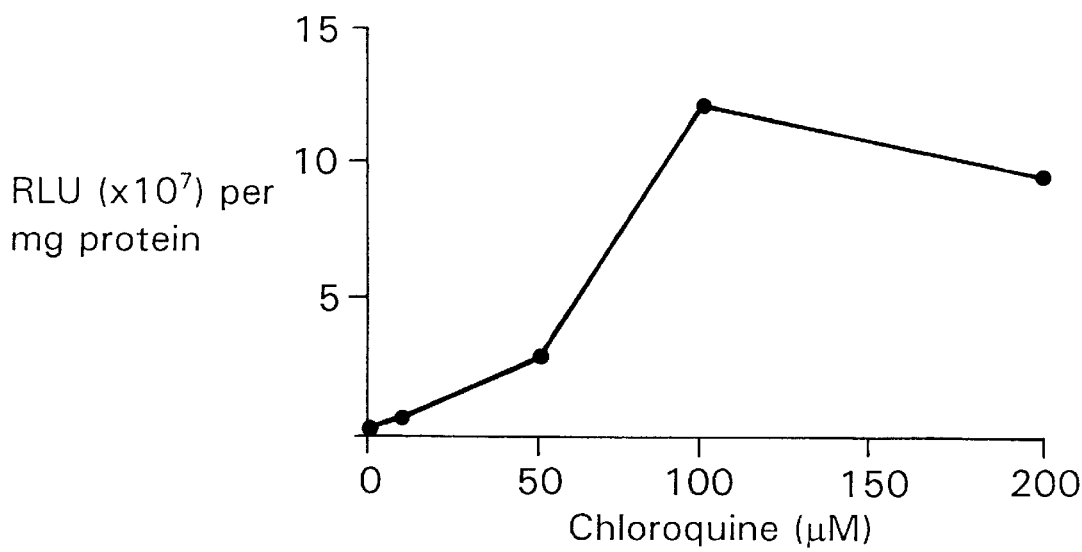
FIG. 5C. Chloroquine at the indicated concentrations was added to the transfection medium containing lactosylated polylysine/pUT 650 complex at a ratio of 3:1 for 4 hours. Cells were washed, incubated in KGM medium for 48 hours, and luciferase activity was measured. In the absence of chloroquine, $2.5 \times 10^6$ RLU per mg of protein was expressed in the cells.

The presence of chloroquine in the transfection mixture containing lactosylated polylysine also resulted in an overall increase in expression of luciferase (FIG. 5C). When chloroquine was absent, luciferase activity was observed to be only 2% of the level observed when 100 μM of chloroquine was added to the transfection mixture.

Transfection of Primary CF Airway Epithelial Cells in Culture

Figure 6A:
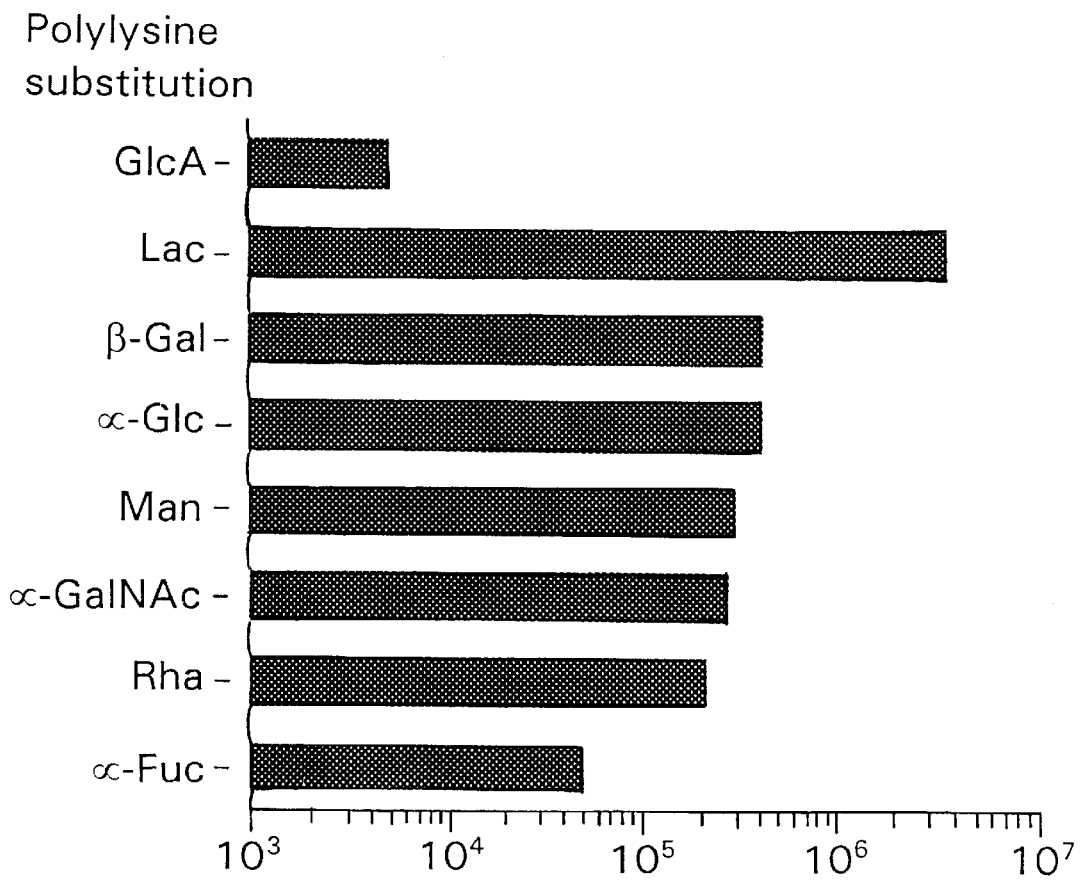
FIG. 6, comprising parts A and B, is a series of graphs depicting reporter gene expression in CF airway epithelial cells in primary culture using glycosylated polylysines as the vehicle. Cells were transfected with glycosylated polylysines complexed with pCMVLuc and the level of gene expression in these cells was compared with that in cells transfected with gluconoylated polylysine complexed with pCMVLuc. Following transfection in the presence of 100 $\mu$M chloroquine, the cells were incubated in LHC-9 medium (Biofluids Inc.) and the amount of luciferase activity expressed in the cells was measured. The results in FIG. 6A and FIG. 6B are those obtained from two separately conducted experiments in two different primary cultures of cells.
Figure 6B:
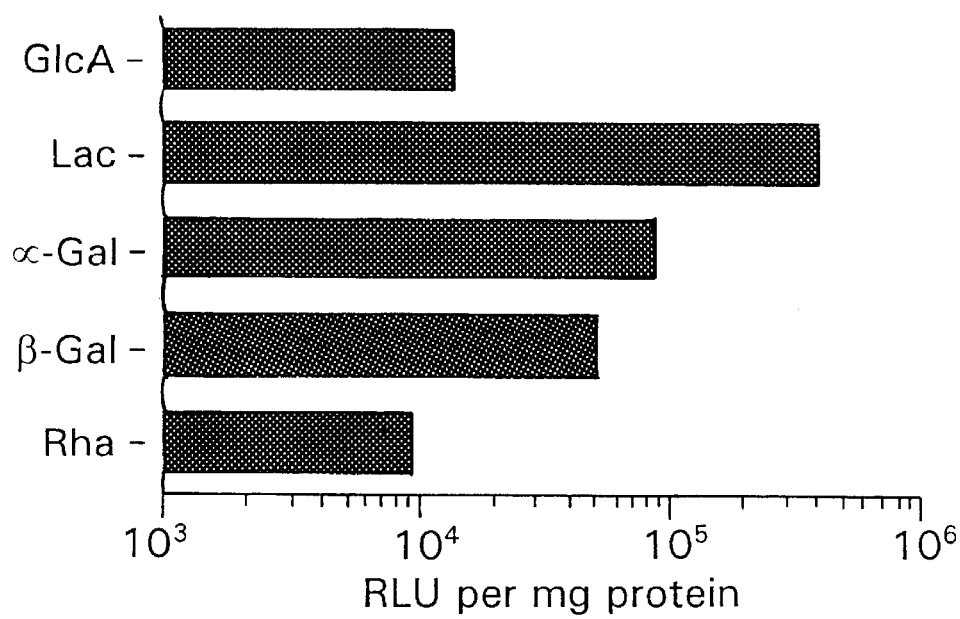

CF airway epithelial cells grown from tracheal tissue explants were transfected and examined for the expression of luciferase using the glycosylated or gluconoylated substituted polylysines as the vehicle and pCMVLuc as the expression plasmid. The results of experiments conducted in two different primary cultures are shown in FIG. 6. A high level of luciferase gene expression was observed when lactosylated polylysine served as the transfection vehicle. Other glycosylated polylysines resulted in approximately 10-fold less luciferase activity in transfected CF cells, and in the case of Fuc-substituted polylysine, luciferase activity was 80-fold less than that observed using lactosylated polylysine.

Figure 7A:
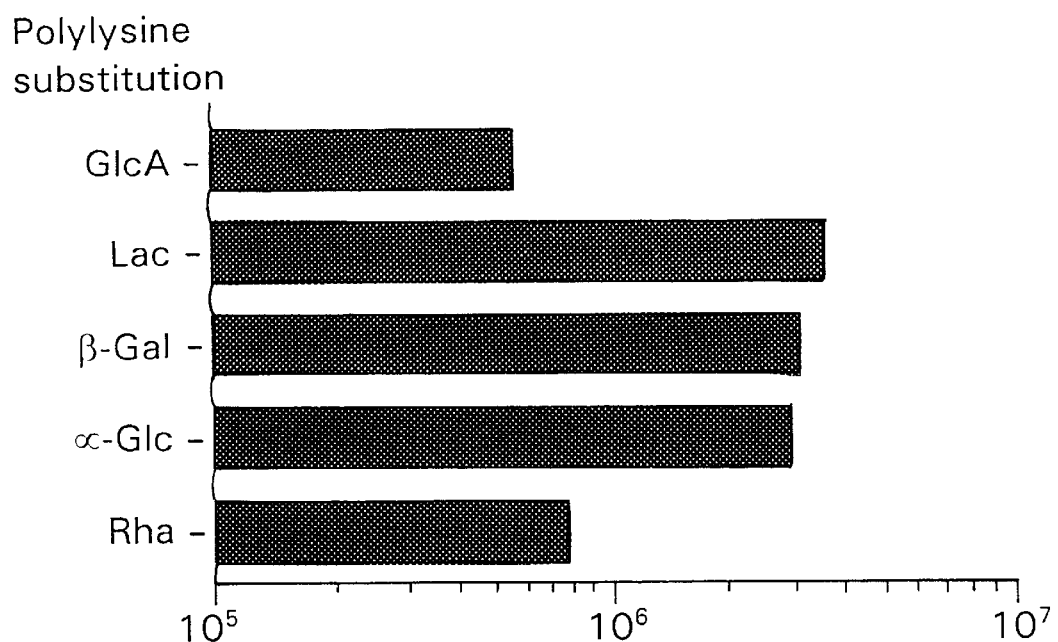
FIG. 7, comprising parts A and B, is a series of graphs depicting reporter gene expression in non-CF tracheal cells in primary culture using glycosylated polylysines as the vehicle. Cells were transfected with glycosylated polylysines complexed with pCMVLuc and the level of gene expression in these cells was compared with that in cells transfected with gluconoylated polylysine complexed with pCMVLuc. Following transfection in the presence of 100 $\mu$M chloroquine, the cells were incubated in LHC-9 medium and the amount of luciferase activity in the cells was measured. The results in FIG. 7A and FIG. 7B are those obtained from two separately conducted experiments in two different primary cultures of cells.

The Use of Glycosylated Polylysines as Vehicles for Transfer of DNA into Primary Human (non-CF) Airway Epithelial Cells Tissue explants were obtained from tracheal tissue which was itself obtained from lung transplant patients. Airway epithelial cells were grown from the tissue explants and were transfected as described herein using a variety of sugar substituted polylysines. These results are shown in FIG. 7.

Figure 7B:
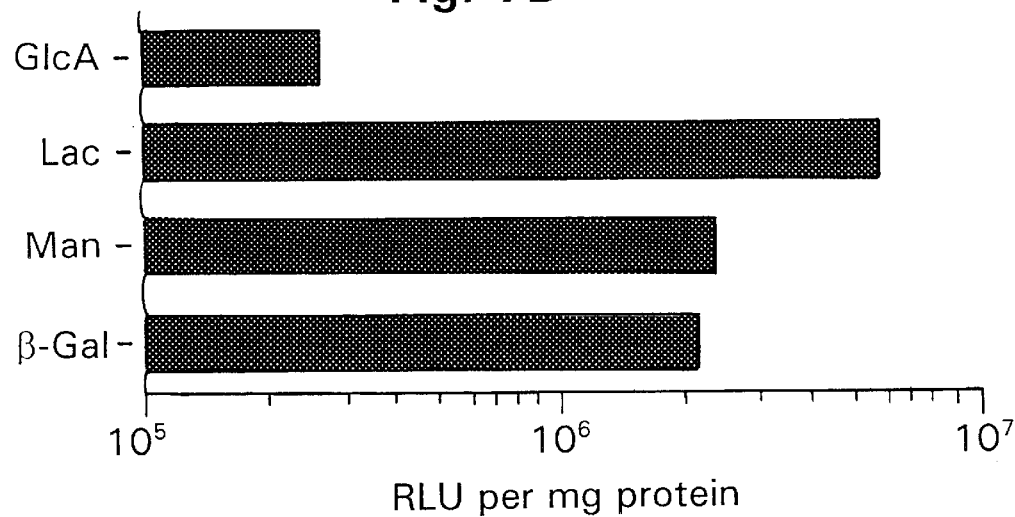

Consistent with the results described above, lactosylated polylysine was an effective vehicle for transfection of non-CF airway epithelial cells (FIG. 7A). α-Glucose- or β-galactose-substituted polylysines were also effective vehicles. In another experiment, galactosylated polylysine proved to be less than 50% as effective for transfection compared with lactosylated polylysine (FIG. 7B). Non-substituted polylysine was only 8% as effective as lactosylated polylysine.

When the time of transfection was increased from 4 to 6 hours, the expression of luciferase was increased by 40% when lactosylated polylysine was used as the transfection vehicle. However, by 8 hours, the transfection efficiency of lactosyl polylysine had decreased, likely due to the fragility of these particular cells and their response to the presence of chloroquine in the transfection medium.

Figure 8:
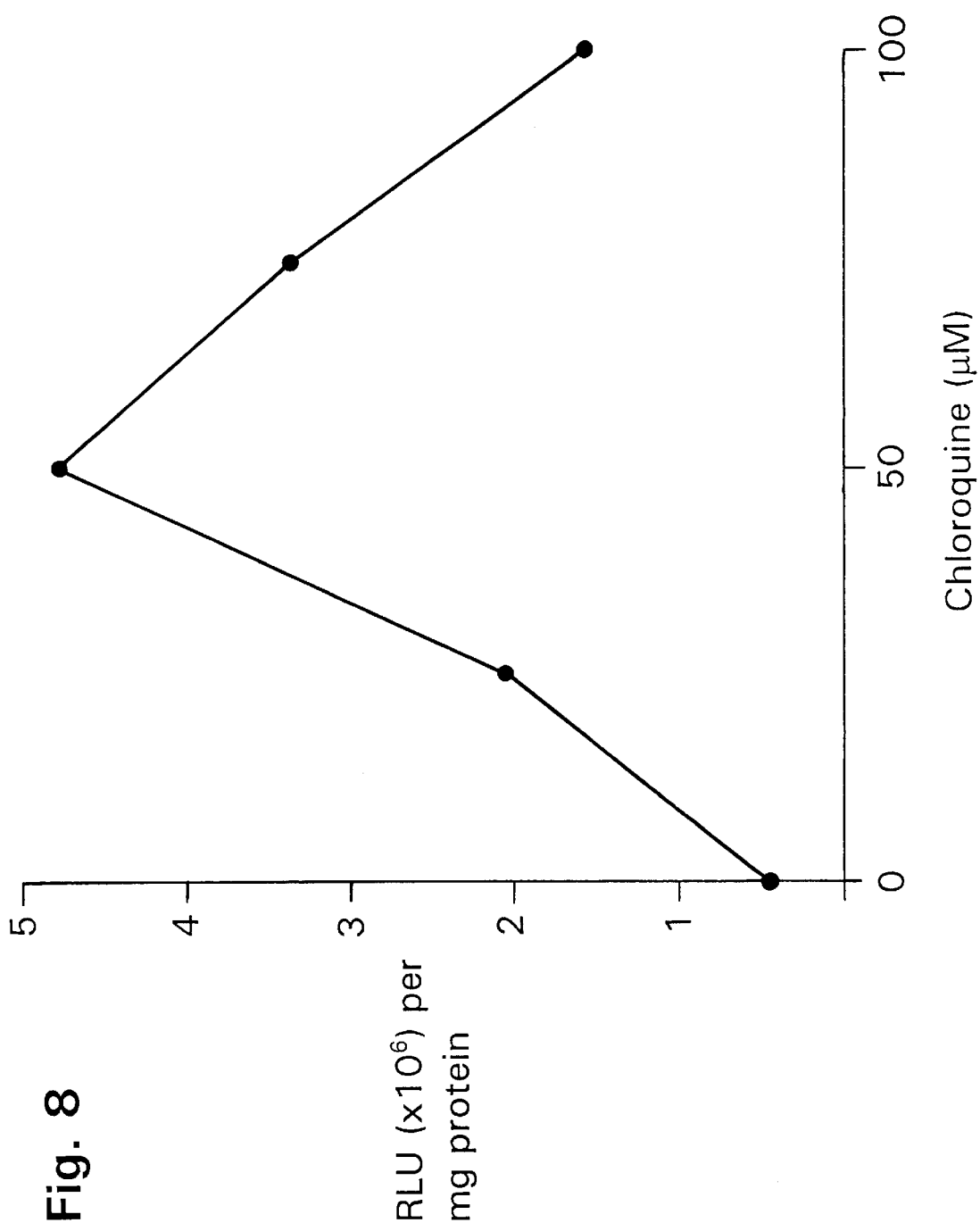
FIG. 8 is a graph depicting the effect of chloroquine on reporter gene expression in non-CF tracheal cells in primary culture. Cells were transfected for 4 hours with lactosylated polylysine and pCMVLuc at a ratio of 3:1 and the indicated concentrations of chloroquine. Following transfection, cells were incubated for 48 hours and the amount of luciferase activity in the cells was subsequently measured.

The concentration of chloroquine required to induce maximum transfection efficiency in human non-CF airway epithelial cells was observed to be lower than that observed in CF/T43 cells (compare FIG.5C and FIG. 8). An optimal level of luciferase expression was observed in primary cells in the presence of 50 μM chloroquine.

In summary, the results just described establish that primary cell cultures (both CF and non-CF) may be efficiently transfected with DNA using glycosylated polylysine as a transfection vehicle. Lactosylated polylysine is superior to other sugar substitutions and gluconoylated polylysine is an inefficient vehicle for gene transfer in these cells.

Endogenous Lectins on CF/T43 Cells Which Bind Lactose

To assess whether the observed enhanced transfection efficiency using lactosylated polylysine is related to any direct interaction between lactosylated polylysine and the carbohydrate binding proteins on the outer surface of the cells, binding studies were conducted. In particular, the binding of lactose- neoglycoprotein was examined.

Figure 9A:
FIG. 9 is a series of photomicrographs depicting binding of Lac-BSA-FITC to CF/T43 cells. CF/T43 cells were grown on coverslips for 24 hours, the culture medium was removed and the cells were processed for the binding assay. Lac-BSA-FITC (100 $\mu$g per ml) was added to the cells for 30 minutes at 4° C. in the absence of (FIG. 9A), and the presence of (FIG. 9B) 0.1 M lactose. The cells were examined in a Nikon Diaphot 300 microscope (Magnification is ×250).
Figure 9B:
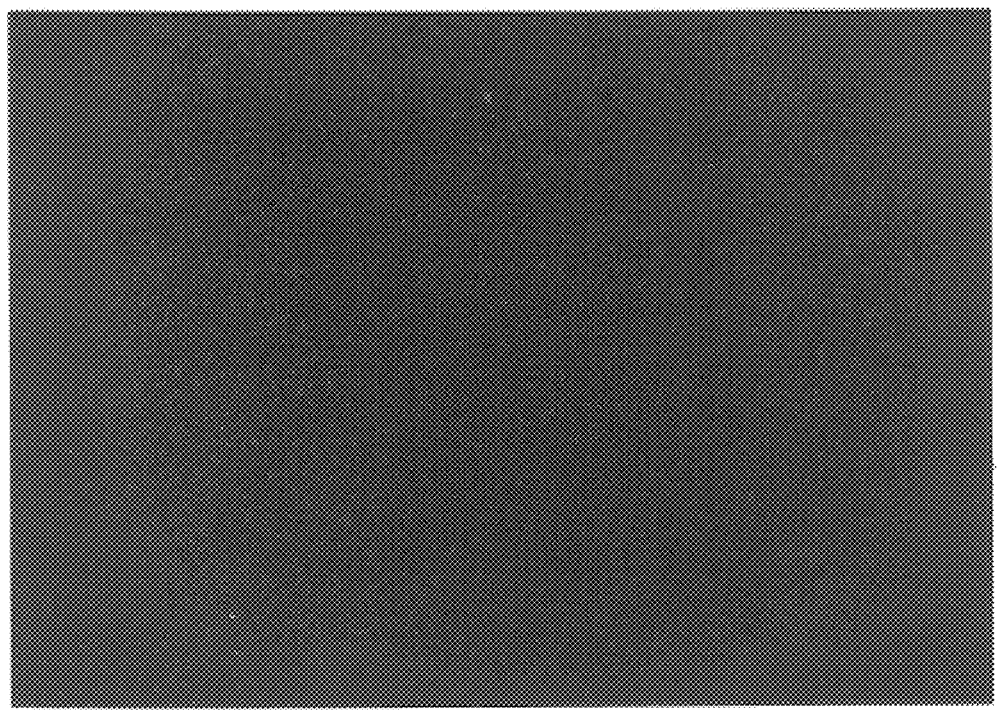

Lactose-neoglycoprotein was prepared by conjugating lactose to BSA-FITC. This compound was added to CF/T43 cells in a binding assay and was observed to bind to the surface of these cells at 4° C. (FIG. 9A). Since binding was blocked by the addition of 0.1 M or 0.2 M lactose, the observed binding was considered to be a specific rather than a non-specific binding of lactose to the cell surface (FIG. 9B). FITC-labeled-BSA did not bind under these conditions. These experiments therefore demonstrate the presence of endogenous lactose-binding lectins on the surface of the airway cells.

In additional experiments, increasing concentrations of lactose added to the transfection medium were observed to effect a decrease in the expression of luciferase. When lactose was added to the transfection medium at a concentration of 0.1 M, a 60% decrease in luciferase expression was observed.

In summary, the data described herein establish that polylysine which is partially substituted with either glycosyl or gluconoyl residues is an effective non-viral vehicle for transfer of DNA into airway epithelial cells. However, glycosylated polylysine, and in particular lactosylated polylysine, is most effective in mediating gene transfer into airway epithelial cells. The presence of chloroquine or other additives as described herein, in the transfection medium enhanced gene transfer in airway epithelial cells even in primary cell cultures.

Thus, according to the present invention, a novel method of transfer of the CF gene into airway epithelial cells has been discovered, which method is useful for treatment of CF. As noted herein, glycosylated polylysines are largely non-immunogenic; thus, they are superior to other non-viral vehicles and are vastly superior to viral vectors as a gene therapy approach for treatment of CF.

Figure 17A:
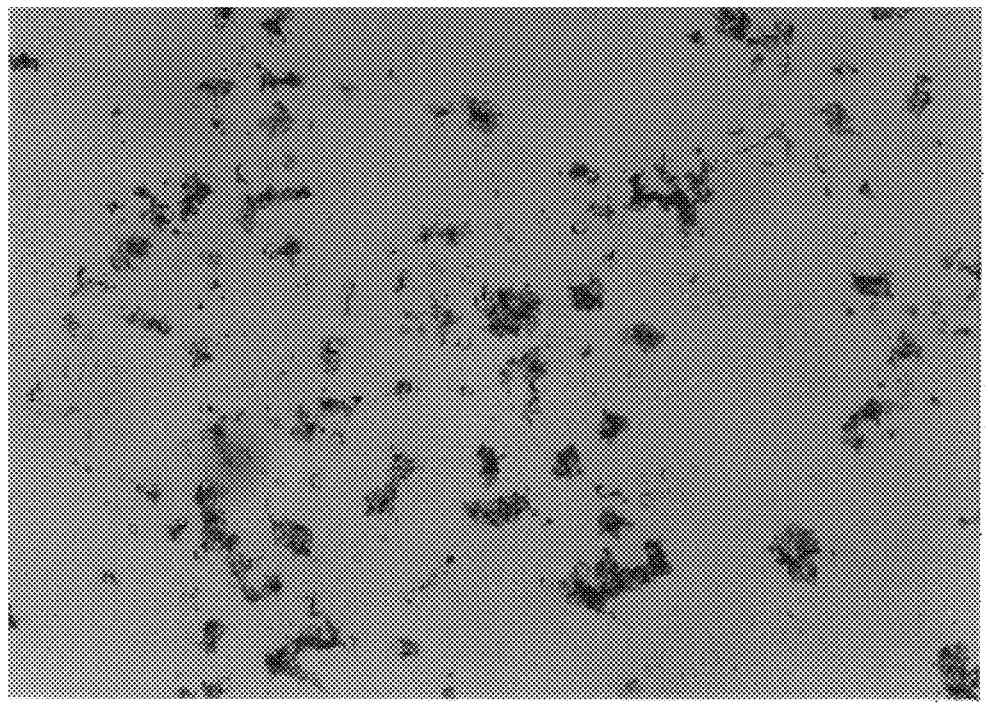
FIG. 17A depicts primary cells grown on coverslips which were transfected with pAdCFTR complexed with lactosylated polylysine.
Figure 17B:
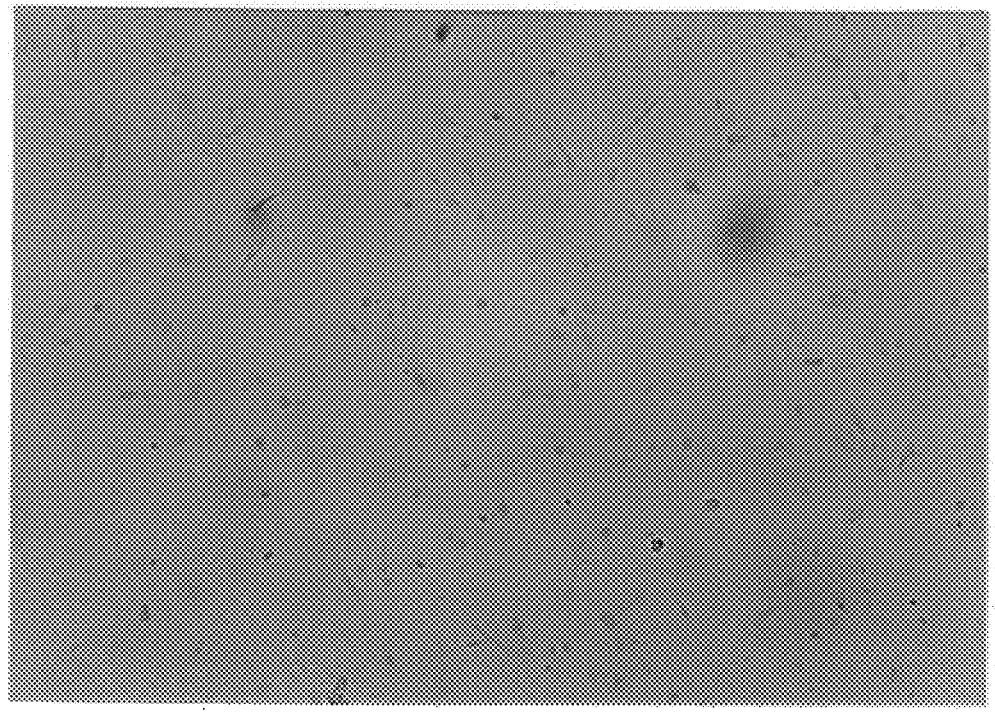
FIG. 17B depicts primary cells grown on coverslips which were transfected with pAdCFTR which was not complexed to lactosylated polylysine.

Transfer of the CFTR Gene into Primary Cells in Culture Using Lactosylated Polylysine as a Delivery Vector The technique of in situ hybridization was used to demonstrate transfer of the CFTR gene into the immortalized cell line, CF/T43, and into cells in primary culture. An example of the results of this type of experiment is shown in FIG. 17. For these studies, cells were grown on coverslips and were transfected with 3 μg of the plasmid, pAdCFTR, or the plasmid, pBQCFTR (Drumm et al., 1990, Cell 62:1227–1233) complexed to 9 μg of lactosylated polylysine. Cells were transfected on three consecutive days in the presence of 5% glycerol and 10 μg fusogenic peptide, in the case of the primary cells, and in the presence of 100 μM chloroquine and 5% glycerol, in the case of the immortalized cells. Other combinations of potentiating agents were also used (Table 1). Expression of CFTR was detected by in situ hybridization using exon 14 of CFTR labeled with deoxygenin as a probe. Labeled or unlabeled cells were visualized in a Nikon Diaphot 300 microscope and the amount of label was quantitated therein.

A variety of control cells, including plasmid which was not complexed with lactosylated polylysine, exhibited about a 25% transfection efficiency. In contrast to the control cells, the transfection efficiency of primary cultures of cells obtained from nasal polyps or trachea was between about 70 and about 90%. The highest transfection efficiency in these cells was accomplished using 5% glycerol and 10 μg of fusogenic peptide in the transfection medium. As shown in Table 1, other combinations of potentiating agents were also used to successfully transfect these cells.

TABLE 1

In situ hybridization of CF cells in primary
culture to detect CFTR mRNA after transfection
with pAdCFTR complexed to lactosylated polylysine

| Additives | CFTR Expressing Cells[a] | | |
|---|---|---|---|
| | High | Medium | Transfected |
| | Percentage of total counted | | |
| None | 22 | 58 | 80 |
| glycerol + Fusogenic peptide[b] | 67 | 22 | 89 |
| Glycerol | 44 | 56 | 100 |
| Chloroquine + Fusogenic peptide | 31 | 68 | 99 |
| Chloroquine | 23 | 66 | 89 |
| Plasmid | 0 | 10 | — |
| Three Additions | | | |
| Glycerol + Fusogenic peptide[b] | 30 | 65 | 95 |
| Glycerol[b] | 35 | 54 | 94 |
| Chloroquine + Fusogenic peptide | 34 | 62 | 91 |

[a]Based on the number of intensely blue (high) or moderately blue (medium) cells.
[b]Average of 2 separate experiments which deviated by 10% or less.

The plasmid/polylysine complex transfected cells may be added to airway epithelial cells as described herein. In addition to assessing expression of CFTR by measuring CFTR-specific mRNA using in situ hybridization, the expression of CFTR in transfected cells may be assessed by measuring the amount of CFTR protein in the cells using any one of the several methods as described herein.

Western blotting analysis may be performed using antibody to the R domain of CFTR as described in Wei et al. (1996, J. Cell. Physiol. 168:373–384) and available technology described for example in Sambrook et al. (Molecular Cloning: A Laboratory Manual, Cold Spring Harbor, N.Y., 1989).

Antibodies are prepared by synthesizing peptides from the deduced amino acid sequence of the R domain and the first ATP binding fold. Peptides may be obtained preferably from regions which are highly conserved between the bovine and human CFTR sequences (Diamond et al., 1991, J. Biol. Chem. 266:22761–22769).

To obtain antibody directed against the R domain of CFTR, peptides including that domain are covalently coupled to tuberculin purified protein derivative (PPD) and are then inoculated into rabbits. Antibody is then purified from serum obtained from the rabbits at periodic intervals. The technology for making antibodies directed against specific peptides is well know in the art and is described for example, in Harlow et al. (1988, In: Antibodies, A Laboratory Manual, Cold Spring Harbor, N.Y.). Antibodies to the C terminus domain of CFTR may also be used (Mulberg et al., 1994, Neuroreport 5:1684–1688).

Alternatively, expression of CFTR may be assessed using a plasmid containing CFTR having a M2-901 epitope tag (Howard et al., 1995, Am J. Physiol. 269:1565–1576). Protein expressed by this plasmid may be detected using M2 antibody which is commercially available (Eastman Kodak Co.) and the methods described by Howard et al. (supra).

The invention further includes administration of chloroquine or other enhancing agent in combination with lactose substituted polylysine CFTR DNA complexes to patients having CF. Administration of chloroquine to humans is known for the prevention of malaria infection. As described herein, chloroquine enhances DNA transfer of sugar substituted polylysine DNA complexes into cells. Thus, administration of this compound in combination with DNA and glycosylated polylysine should serve to enhance transfection of airway epithelial cells in a safe and effective manner.

The amount of chloroquine to be included in the transfection mixture for administration to humans or animals may vary from about 25 $\mu$M to about 200 $\mu$M per dose. Preferably, the amount of chloroquine to be included in the mixture is from about 50 $\mu$M to about 100 $\mu$M.

Other enhancing agents may be used in the transfection mixture in place of or in addition to chloroquine. Such agents include, but are not limited to, bioactive peptides and glycerol. Suitable peptides include, but are not limited to, E5CA-GLFEAIAEFIEGGWEGLIEGCA (Midoux et al., 1993, Nucleic Acids Res. 21:871–878), HA-2-GLFEAIAGFIENGWEGMIDGGGC (Wagner et al., 1992, Proc. Natl. Acad. Sci. USA 89:7934–7938) and JTS-1-GLFEALLELLESLWELLLEA (Gottshalk et al., 1996, Gene Ther. 3:448–457).

Examples of the enhancement of transfection by glycerol and the fusogenic peptide ESCA are now described.

Figure 10:
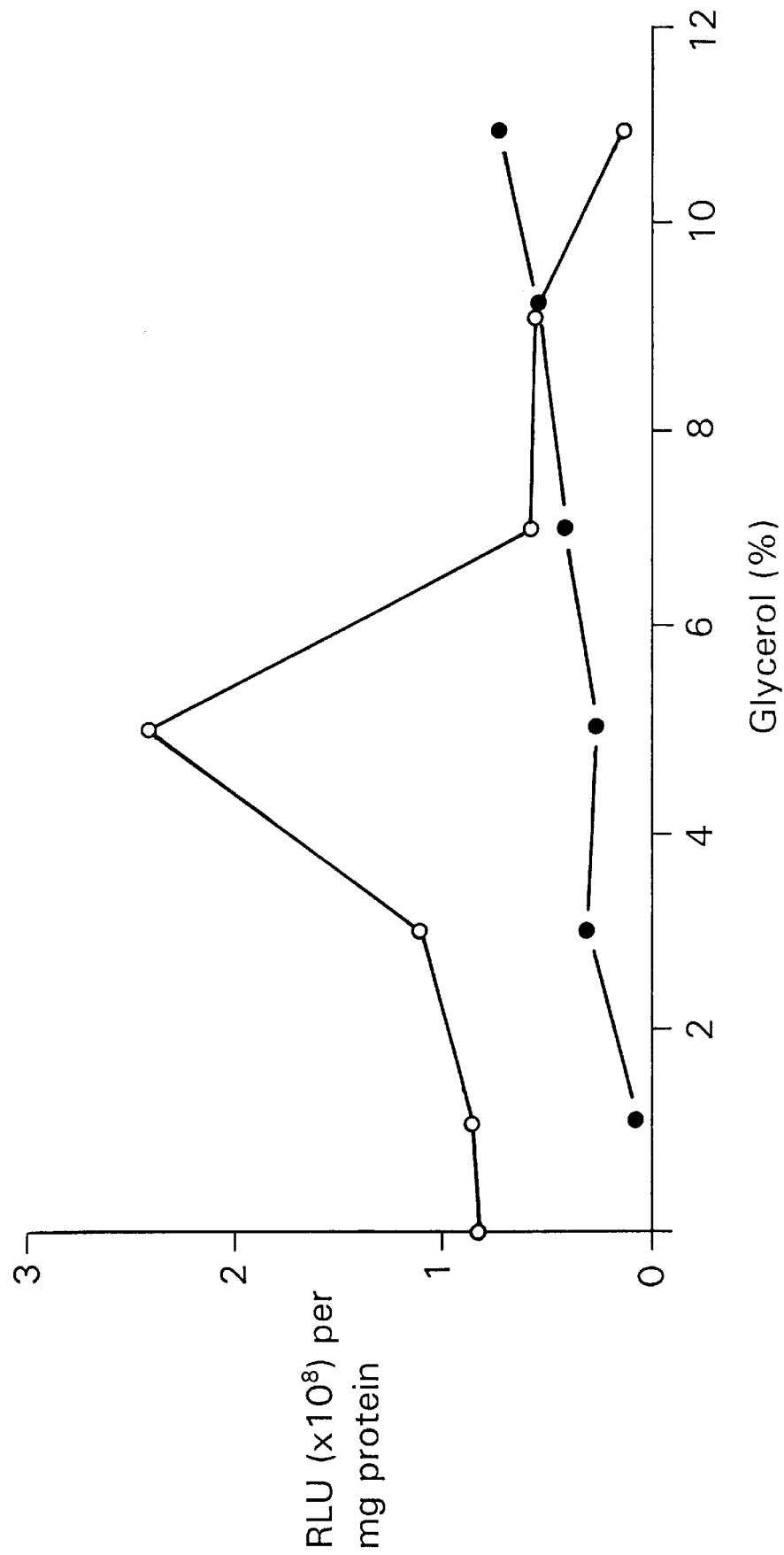
FIG. 10 is a graph depicting enhancement of reporter gene expression in CF/T43 cells transfected with a plasmid encoding the reporter gene, pCMVLuc, complexed to lactosylated polylysine, wherein the transfection was conducted in the presence (open circles) or absence (closed circles) of 100 μM chloroquine and the indicated concentrations of glycerol.
Figure 11:
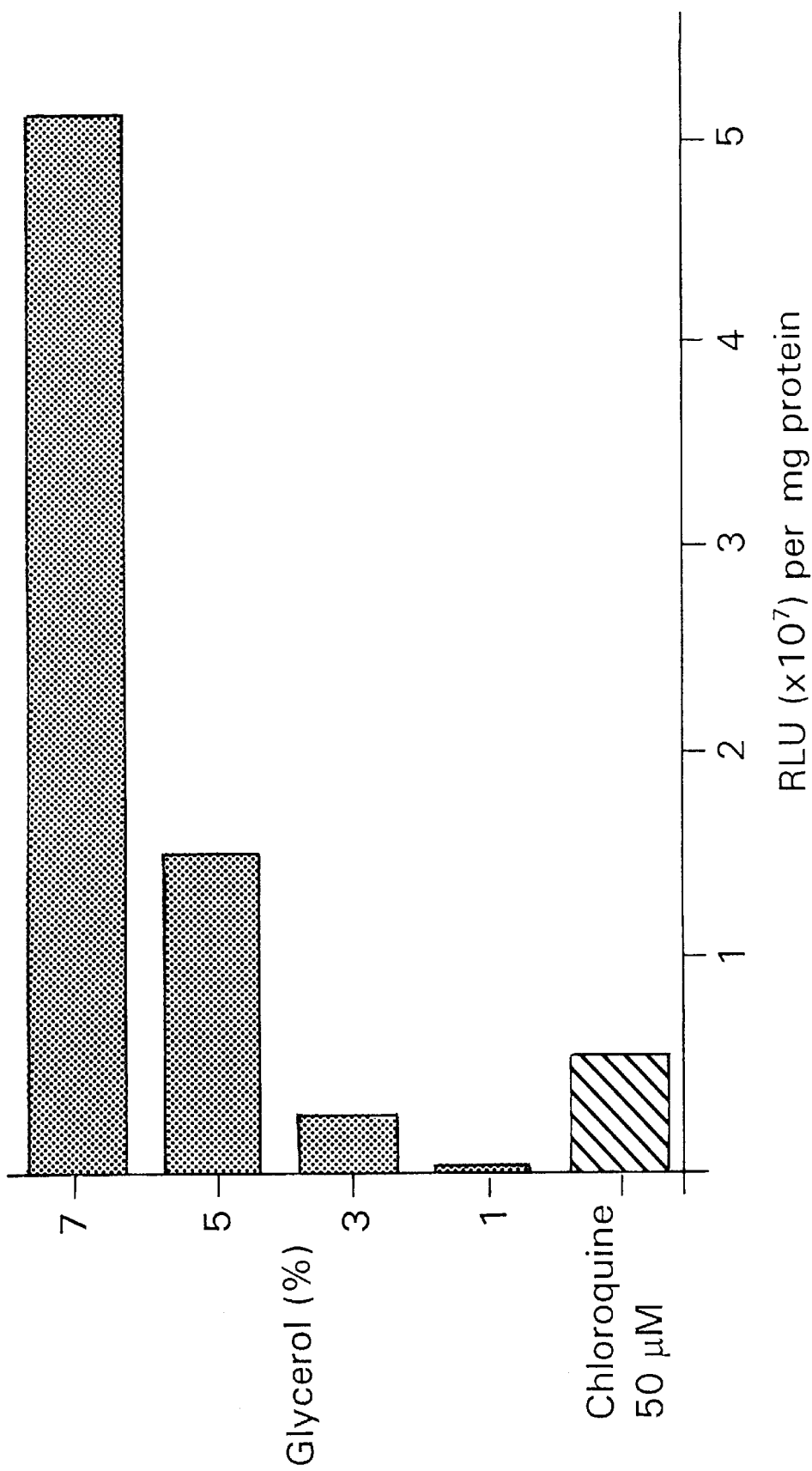
FIG. 11 is a graph depicting enhancement of reporter gene expression in primary airway epithelial cells transfected with a plasmid encoding the reporter gene, pCMVLuc, complexed to lactosylated polylysine, wherein the transfection was conducted in the presence of the indicated concentrations of glycerol without the addition of chloroquine. A transfection assay conducted in the presence of 50 μM chloroquine was used for comparison.

Cells were transfected with pCMVLuc complexed to lactosylated polylysine in the presence or absence of glycerol and/or chloroquine. Following a four hour incubation period with the transfection mixture, the cells were treated as described herein and were incubated for a further 48 hours. The cells were then lysed and luciferase activity expressed therein was assessed as described herein. It is evident from the data shown in FIGS. 10 and 11 that glycerol enhances transfection of both CF/T43 cells and primary airway epithelial cells when the cells are transfected either with or without chloroquine.

Figure 12:
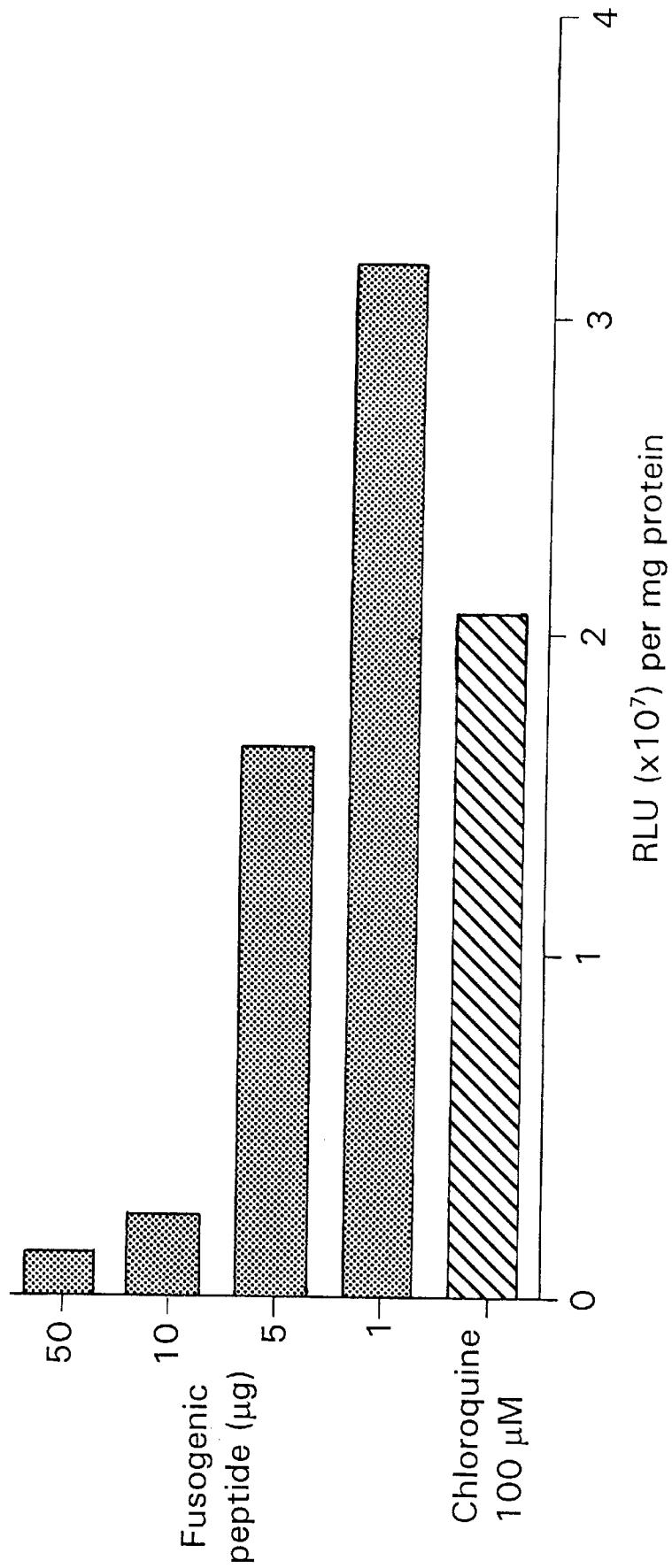
FIG. 12 is a graph depicting enhancement of reporter gene expression in CF/T43 cells transfected with a plasmid encoding the reporter gene, pCMVLuc, complexed to gluconoylated polylysine, in the presence of the indicated concentrations of fusogenic peptide or chloroquine.
Figure 13:
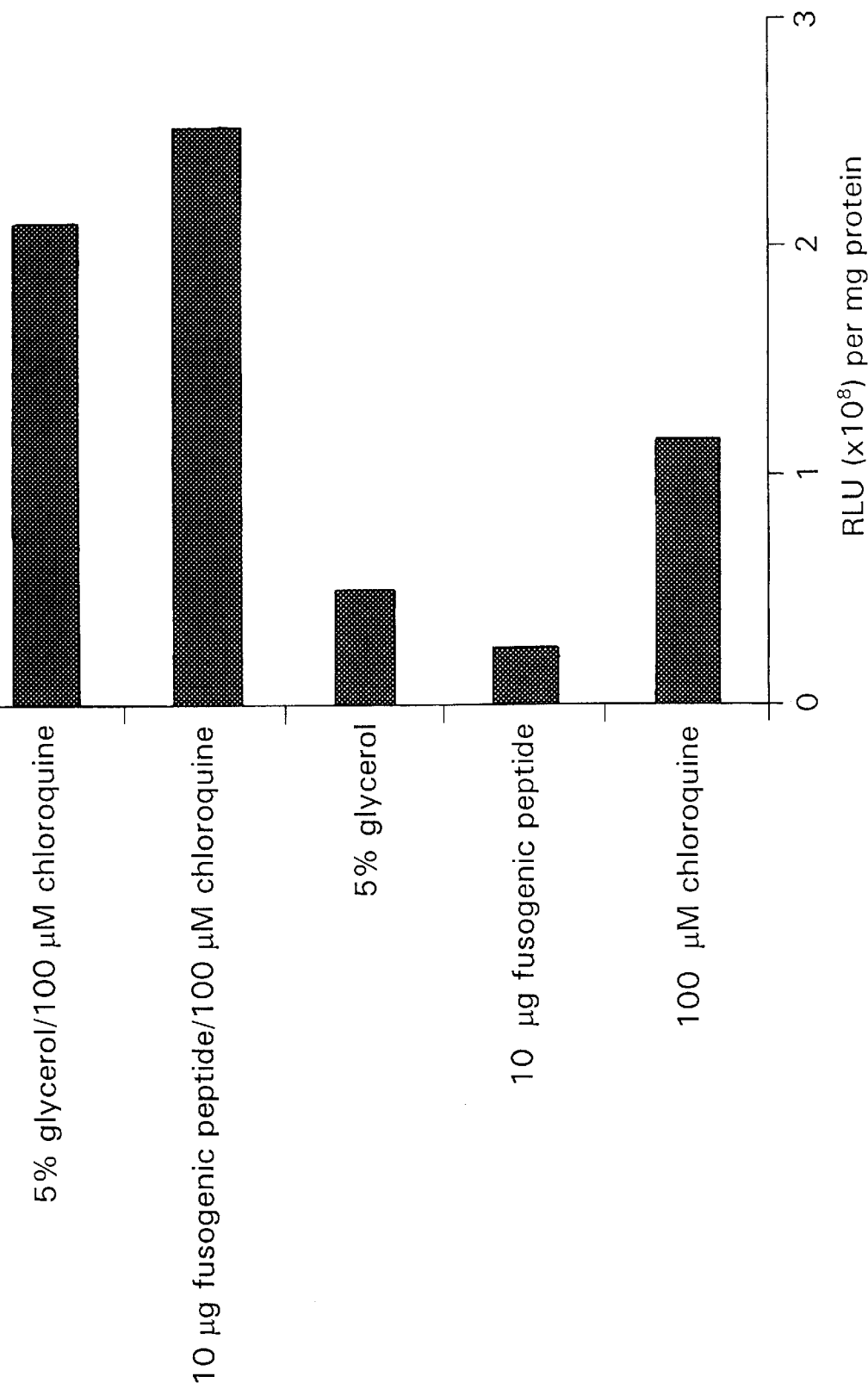
FIG. 13 is a graph depicting the enhancement of reporter gene expression in CF/T43 cells transfected with a plasmid encoding the reporter gene pCMVLuc coupled to lactosylated polylysine in the presence of the indicated concentrations of different additives as noted.

In a similar manner to that just described, CF/T43 cells were transfected for three hours with a reporter gene complexed to gluconoylated polylysine in the presence of increasing amounts of the fusogenic peptide, E5CA. The results of these experiments are shown in FIG. 12. It is evident that the transfection efficiency of the cells was markedly enhanced in the presence of fusogenic peptide. The enhancement of luciferase gene expression in CF/T43 cells transfected with a lactosylated polylysine DNA complex is summarized in FIG. 13.

Several other immortalized cell lines were examined to determine the effect of the potentiating agents in increasing the efficacy of transfection of cells. The cells used comprised BEAS2B cells which are immortalized epithelial cells obtained from a non-CF patient (Reddell et al., 1988, Cancer Res. 48:1904–1909). CF/T1 (wild type) immortalized airway cells were also used. These cells were obtained from a CF patient having the $\Delta$F508 mutation which had been previously transfected with wild type CFTR (Olsen et al., 1992, Hunam Gene Therapy 3:253–266). Both of these cells were transfected as described herein in the presence or absence of various additives as indicated in FIG. 18. In each case, the cells responded to the additives in a similar manner wherein 50 or 100 $\mu$M of chloroquine and 5% glycerol yielded the greatest increase in transfection efficiency as measured by expression of luciferase in transfected cells.

The data presented herein establish that the invention can be construed to include transfection mixtures having additional compounds added thereto, which compounds serve to enhance the transfection efficiency of the desired cells. Glycerol or a fusogenic peptide may be added to the transfection mixture, either before, concurrently or following addition of the DNA to the cells.

Examination of the Efficiency of Gene Expression

Figure 16A:
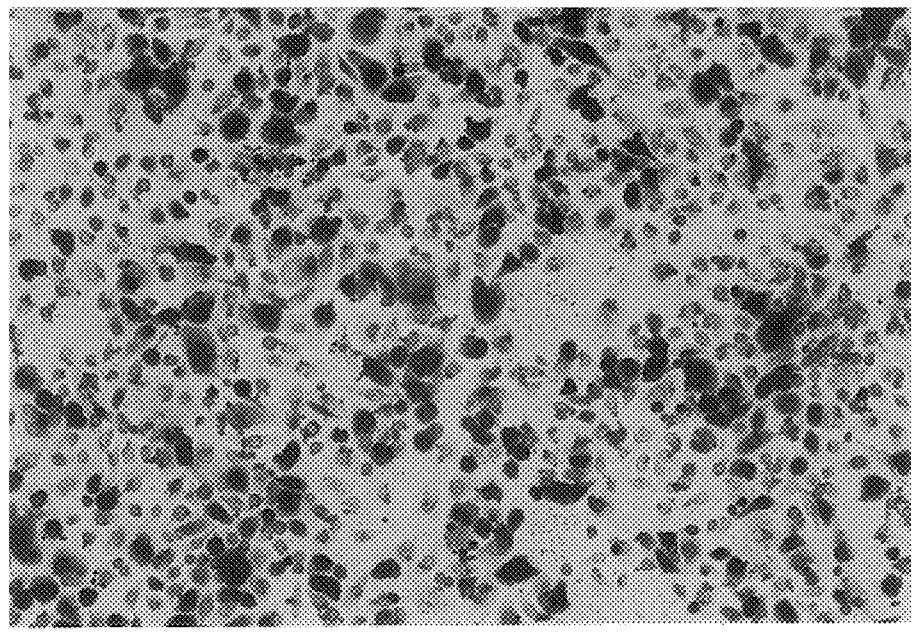
FIG. 16A is an image of cells transfected with pCMVLacZ coupled to lactosylated polylysine, wherein the cells were transfected for three consecutive days.
Figure 16B:
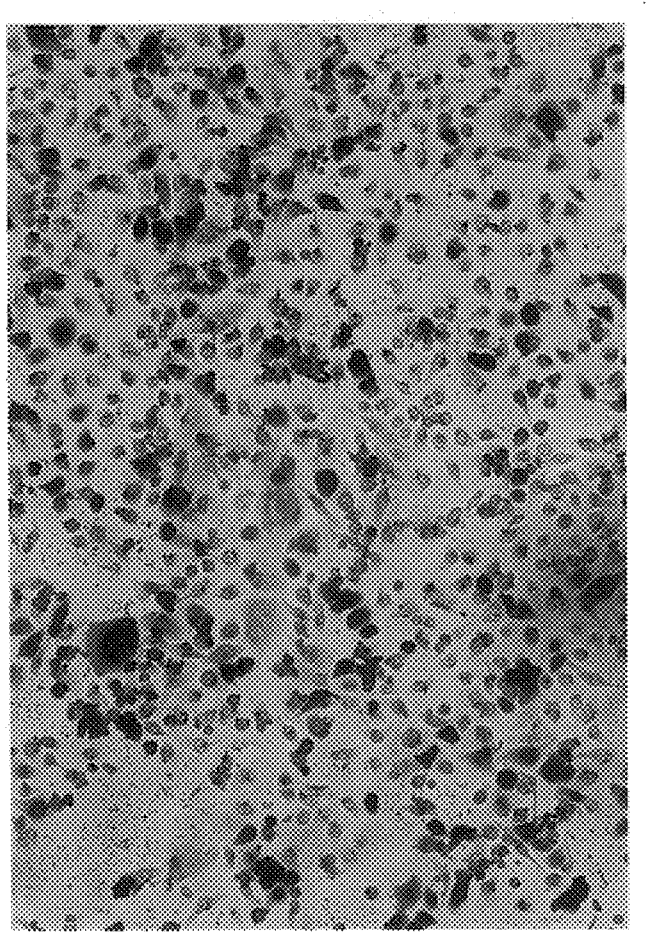
FIG. 16B is an image of cells transfected as in FIG. 16A, wherein the cells were transfected once.
Figure 16C:
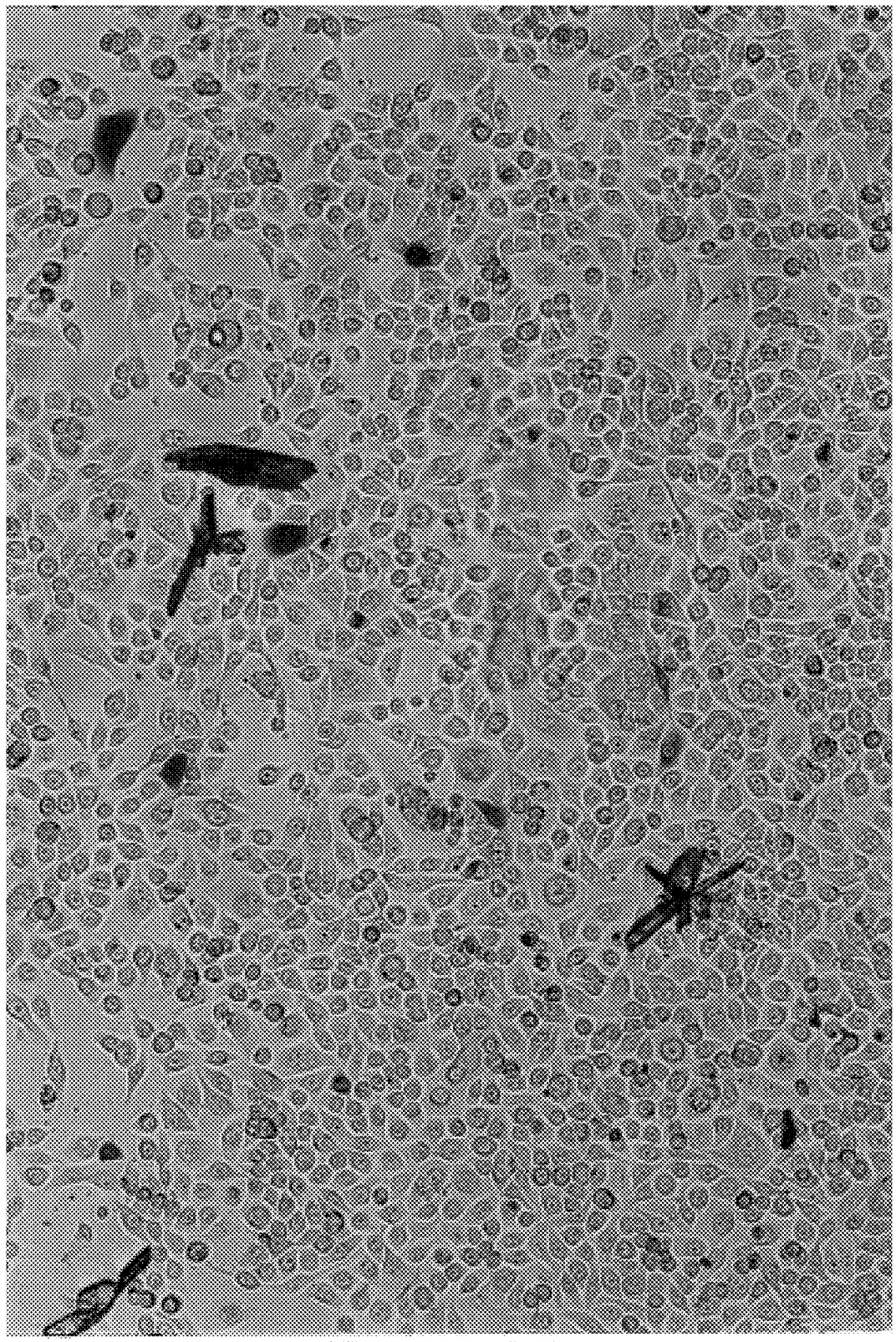
FIG. 16C is an image of cells transfected as in FIG. 16A, wherein the cells were transfected with the plasmid but without lactosylated polylysine.

In experiments designed to examine the efficiency of gene expression, the reporter gene, pCMVLacZ complexed to lactosylated polylysine was used. Cells were transfected with the reporter gene and expression of the gene was assessed by staining the cells with X-gal. The results of a typical experiment of this type are presented in FIG. 16. Approximately 40% of the cells exhibited intense blue staining. After three subsequent transfections, 90% of the cells exhibited moderate to intense blue staining which was not evident in control untransfected cells. These experiments establish that CF/T43 cells may be transfected with high efficiency using the composition of the invention as described herein.

Figure 15A:
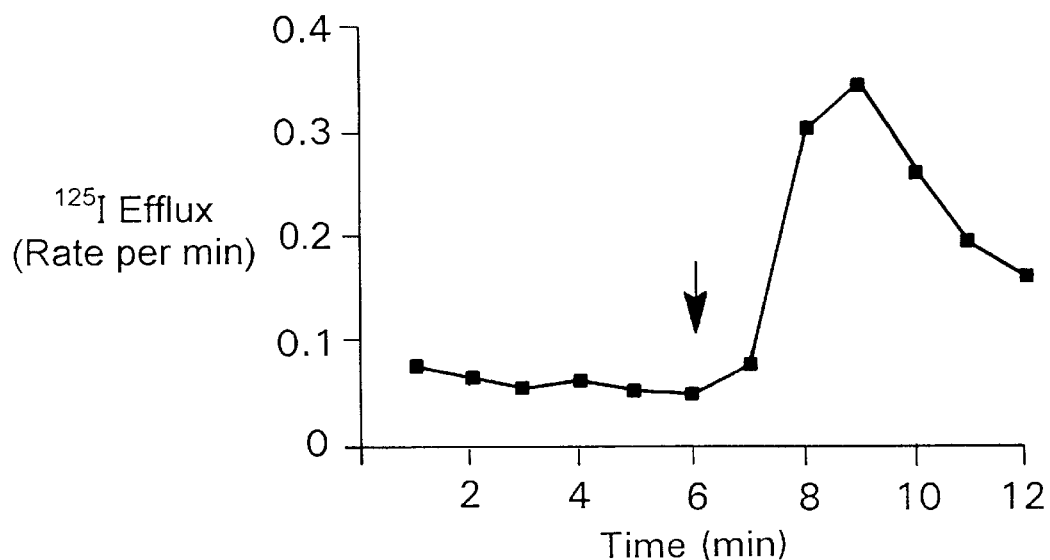
FIG. 15A (Panel A) comprises data obtained from T-84 tumor cells which are the prototype of CFTR-containing cells.
Figure 15B:
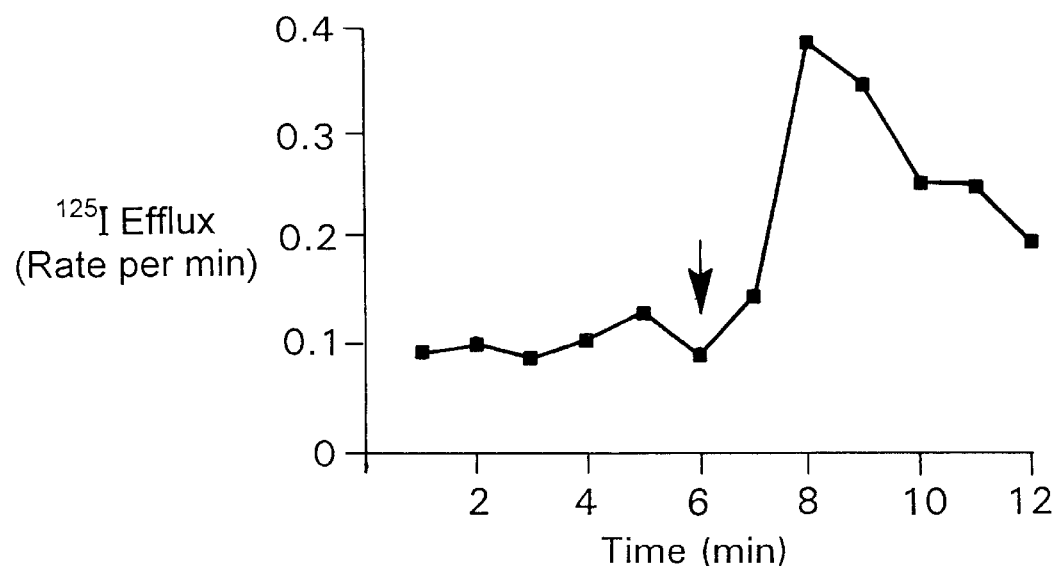
FIG. 15B (Panel B) comprises data obtained from CFT1 cells whose defect has been corrected by the addition of wild type CFTR. CF/T43 cells exhibited no response when similarly treated.

Assessment of Whether Transfection of the CFTR Gene Results in Functional Correction of the CF Defect in Airway Epithelial Cells (A) Measurement of $^{125}$I-efflux from CF/T43 cells (FIG. 15). $^{125}$I-efflux from cultured CF cells is a measure of whether the CFTR defect in cells has been corrected, wherein correction of the defect results in an increase in efflux of $^{125}$I. $^{125}$I-efflux is measured in a manner similar to that described by Marks et al. (1988, 10th *International CF Congress*, Sydney, Australia). Essentially, immortalized CF airway epithelial cells (CF/T43) and primary CF and non-CF airway epithelial cells are transfected with the lactosylated polylysine/CFTR plasmid complex using the transfection conditions described herein. The cells are seeded in 35 mm dishes at a cell concentration of $10^6$ cells per dish. Chloride channel activity in the presence of additives such as forskolin, is assayed by measuring the rate of $^{125}$I-efflux (Venglarik et al., 1990, *Am. J. Physiol.* 259:C358–C364; Santos et al., 1994, *Biochim. Biophys. Acta* 1195:96–102; Drumm et al., 1990, *Cell* 62:1227–1233).

(B) Measurement of SPQ fluorescence. Immortalized CF airway epithelial cells (CF/T43) and primary CF and non-CF airway epithelial cells are cultured on glass coverslips and are transfected with the lactosylated polylysine/CFTR plasmid complex as described herein. Following transfection, the cells are further incubated for 36–48 hours. The cells are then washed with PBS and the halide sensitive fluorophore 6-methoxy-N-(3-sulphopropyl)quinolinium (SPQ) is added. The cells are analyzed according to the method of Yang et al. (1993, *Hum. Mol. Gen.* 8:1253–1261). SPQ fluorescence is quantitated and any increase in fluorescence is an indication that the CFTR defect in the cells has been corrected.

The results of experiments designed to measure CFTR activity by assessing the Cl$^-$ activity of the protein by $^{125}$I efflux in the presence of the described stimulants, are presented in FIG. 15. In this experiment, T-84 cells expressing cells were examined and exhibited a Cl$^-$ efflux rate per minute of 3–4 (FIG. 15, Panel A). CF/T1 cells whose defect was corrected by the addition of wild type CFTR, also exhibited an efflux rate which was similar to the response of T-84 cells (FIG. 15, Panel B). As expected, CF/T43 cells exhibited no response to the stimulation mixture.

Transfer of Reporter Genes into Airway Epithelial Cells in Animals

Adult C57/BL6 mice provide an effective animal model for testing the efficacy of glycosylated polylysine vehicles for gene transfer into respiratory epithelial cells in vivo. Each of the glycosylated polylysines described herein may be examined in this model for the ability to efficiently transfer DNA into airway epithelial cells in vivo as follows.

The glycosylated polylysine is combined with the reporter plasmid CMV-LacZ (CAYLA or other supplier) as described. Aliquots of 100 μl containing 2–10 μg of plasmid are administered to anesthetized mice via the intranasal or intratracheal route. This method is successful when adenoviral vectors are used and results in reliable gene expression in distal airway and parenchymal cells. One, three, or six doses are administered to the animals intranasally on sequential days. The animals are sacrificed two days following the last dose and are processed for histopathology and β-galactosidase expression. Controls may include recombinant adenoviral vectors (AdCMVLacZ/sub360) to assess cell specificity and distribution of transgene expression (St. George et al., 1995, "Efficacy of Adenoviral Vectors in Airway Epithelium" Cystic Fibrosis Conference, Abstract#151). Newborn lung and fetal lungs from animals may also be tested using the methods described herein.

Transfer of the CFTR Gene into Animals.

CFTR-encoding plasmids are complexed with glycosylated polylysine and are administered to an animal following the procedures just described for transfer of reporter plasmids to animal airway epithelial cells. Expression of CFTR is detected as described herein. Administration of lactose substituted polylysine to the airway cells of animals may be accomplished by aerosol through the nasal passages, by bronchoscopy or by any other method available in the art, such as by tracheal catheter.

In addition to mice, rabbits and other vertebrate animals may be used, including non-human primate animals, to examine the introduction of CFTR into the airway epithelial cells of these animals using the methods described herein.

Assessment of In Vivo Correction of the CF Defect in Animal Models

The tracheal xenograft model may be used for these studies. To assess correction of the CF defect in vivo, immune incompetent mice which have been given a denuded rat-trachea transplant under the skin on which CF airway epithelial cells are grafted are used. Aliquots of 100 μl of plasmid/polylysine complex plus 50 μM chloroquine are administered to the animals at the site of the xenograft. After about 4 hours, the mixture is removed and correction of the CF-associated transepithelial potential difference with amiloride stimulation is measured after 36–40 hours post transfection.

Alternatively, any of the other animals discussed herein may also be used for administration of CFTR.

As discussed herein, the invention should also be construed to include treatment of CF in utero using lactose substituted polylysine DNA complexes.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of transfecting airway epithelial cells comprising adding to said cells a composition comprising a complex comprising an isolated nucleic acid and a glycosylated polylysine, said composition further comprising at least one of chloroquine, glycerol, and a fusogenic peptide.

2. The method of claim 1, wherein said cells are transfected in vitro.

3. The method of claim 1, said glycosylated polylysine having a sugar component selected from the group consisting of lactose, α-glucose, β-galactose, mannose, mannose-6-phosphate, fucose and N-acetylglucosamine.

4. The method of claim 3, wherein said glycosylated polylysine is lactosylated polylysine.

5. The method of claim 1, wherein said isolated nucleic acid is DNA.

6. The method of claim 5, wherein said DNA is selected from the group consisting of DNA encoding CFTR, an asthma gene, DNA encoding α1AT, a gene affecting idiopathic pulmonary fibrosis, DNA encoding SP-B and DNA encoding SP-C.

7. The method of claim 6, wherein said DNA encodes CFTR.

8. The method of claim 5, wherein said DNA is cDNA.

9. An in vitro cell transfection kit comprising a selection of glycosylated polylysines and instructions for using said kit.

10. The kit of claim 9, further comprising a reporter DNA.

11. The kit of claim 10, wherein said reporter DNA is selected from the group consisting of a chloramphenicol acetyl transferase gene, a luciferase gene, a green fluorescent protein gene, and a β-galactosidase gene.

12. The kit of claim 9, further comprising at least one of chloroquine, glycerol and a fusogenic peptide.

13. The kit of claim 9, said glycosylated polylysine having a sugar component selected from the group consisting of lactose, α-glucose, β-galactose, mannose, mannose-6-phosphate, fucose and N-acetylglucosamine.

14. A lactosylated polylysine nucleic acid complex comprising DNA encoding CFTR, or a biologically active fragment thereof, and lactosylated polylysine, wherein the weight to weight ratio of lactosylated polylysine to said DNA in said complex is about one to one to about fifteen to one, and further wherein said complex comprises at least one of chloroquine, glycerol and a fusogenic peptide, said complex being capable of transfecting airway epithelial cells when added thereto.

15. The lactosylated polylysine nucleic acid complex of claim 14, wherein the weight to weight ratio of lactosylated polylysine to said DNA encoding CFTR in said complex is about nine to one.

16. A method of transfecting airway epithelial cells, said method comprising generating a composition comprising a complex comprising an isolated nucleic acid and a glycosylated polylysine, said composition further comprising at least one of chloroquine, glycerol and a fusogenic peptide, and adding said complex to said airway epithelial cells.

17. The method of claim 16, said glycosylated polylysine having a sugar component selected from the group consisting of lactose, α-glucose, β-galactose, mannose, mannose-6-phosphate, fucose and N-acetylglucosamine.

18. The method of claim 17, wherein said glycosylated polylysine is lactosylated polylysine.

19. The method of claim 16, wherein said cells are transfected in vitro.

20. The method of claim 16, wherein said isolated nucleic acid is DNA.

21. The method of claim 20, wherein said DNA is cDNA.

22. A The method of claim 20, wherein said DNA is selected from the group consisting of DNA encoding CFTR, an asthma gene, DNA encoding α1AT, a gene affecting idiopathic pulmonary fibrosis, DNA encoding SP-B and DNA encoding SP-C.

23. The method of claim 22, wherein said DNA encodes CFTR.

24. A kit comprising an isolated nucleic acid encoding CFTR, or a biologically active fragment thereof, a glycosylated polylysine and instructions for using said kit for transfection of airway epithelial cells.

25. An airway epithelial cell transfected with a complex comprising at isolated nucleic acid and a glycosylated polylysine, said complex further comprising at least one of chloroquine, glycerol and a fusogenic peptide.

26. The airway epithelial cell of claim 25, wherein said isolated nucleic acid is DNA encoding CFTR and said glycosylated polylysine is lactosylated polylysine.

27. A composition for transfection of airway epithelial cells comprising a complex comprising an isolated nucleic acid and a lactosylated polylysine, said composition further comprising at least one of chloroquine, glycerol and a fusogenic peptide, wherein said isolated nucleic acid is DNA selected from the group consisting of DNA encoding CFTR, an asthma gene, DNA encoding α1AT, a gene affecting idiopathic pulmonary fibrosis, DNA encoding SP-B and DNA encoding SP-C.

28. The composition of claim 27, wherein said DNA is DNA encoding CFTR.

29. The composition of claim 28, wherein said airway epithelial cells are transfected in vitro.

\* \* \* \* \*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

```
Gly Leu Phe Glu Ala Ile Ala Glu Phe Ile Glu Gly Gly Trp Glu Gly
1               5                  10                  15

Leu Ile Glu Gly Cys Ala
            20
```

(2) INFORMATION FOR SEQ ID NO:2:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

```
Gly Leu Phe Glu Ala Ile Ala Gly Phe Ile Glu Asn Gly Trp Glu Gly
1               5                  10                  15

Met Ile Asp Gly Gly Gly Cys
            20
```

(2) INFORMATION FOR SEQ ID NO:3:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

```
Gly Leu Phe Glu Ala Leu Leu Glu Leu Leu Glu Ser Leu Trp Glu Leu
1               5                  10                  15

Leu Leu Glu Ala
            20
```